US012193688B2

(12) United States Patent
Nguyen et al.

(10) Patent No.: US 12,193,688 B2
(45) Date of Patent: *Jan. 14, 2025

(54) SYSTEMS AND METHODS FOR CO-OPERATIVE CONTROL OF ROBOTICALLY-POSITIONED SURGICAL INSTRUMENTS

(71) Applicant: Orthosoft ULC, Montreal (CA)

(72) Inventors: Trong-Tin Nguyen, Laval (CA); Karine Dupuis, Montreal (CA); Jeremie Menard, Montreal (CA); Chloe Landry, Saint-Jean-sur-Richelieu (CA)

(73) Assignee: Orthosoft ULC, Montreal (CA)

( * ) Notice: Subject to any disclaimer, the term of this patent is extended or adjusted under 35 U.S.C. 154(b) by 0 days.

This patent is subject to a terminal disclaimer.

(21) Appl. No.: 18/477,030

(22) Filed: Sep. 28, 2023

(65) Prior Publication Data

US 2024/0023977 A1 Jan. 25, 2024

Related U.S. Application Data

(62) Division of application No. 17/185,529, filed on Feb. 25, 2021, now Pat. No. 11,801,062.

(Continued)

(51) Int. Cl.
*A61B 17/17* (2006.01)
*A61B 17/00* (2006.01)
(Continued)

(52) U.S. Cl.
CPC ............. *A61B 17/17* (2013.01); *A61B 34/30* (2016.02); *A61B 90/50* (2016.02); *A61B 2017/00477* (2013.01); *A61B 2034/2072* (2016.02)

(58) Field of Classification Search
CPC ......... A61B 17/17; A61B 34/30; A61B 90/50; A61B 2034/2072; A61B 2017/00477
See application file for complete search history.

(56) References Cited

U.S. PATENT DOCUMENTS 7,670,343 B2 * 3/2010 Meridew ............ A61B 17/1746
606/81
8,884,618 B2 11/2014 Mahfouz
(Continued)

FOREIGN PATENT DOCUMENTS

AU 2021232216 2/2024
AU 2021232216 B2 2/2024
(Continued)

OTHER PUBLICATIONS

"U.S. Appl. No. 17/185,529, Non Final Office Action mailed Mar. 16, 2023", 12 pgs.
(Continued)

*Primary Examiner* — Kevin T Truong
*Assistant Examiner* — Diana Jones
(74) *Attorney, Agent, or Firm* — SCHWEGMAN LUNDBERG & WOESSNER, P.A.

(57) ABSTRACT

A reamer attachment system for attaching a reamer to a robotic arm comprises a reaming guide comprising a guide shaft and a collar attached to the guide shaft, a reamer shaft extending through the collar to articulate against the collar, and a reamer lock couplable to the reamer shaft to engage the collar and prevent axial displacement of the reamer shaft relative to the collar while permitting the reamer shaft to articulate against the collar. A method for collaborative reaming of a bone between a surgical robot and a surgeon comprises positioning a reamer guide at a location in a coordinate system for the surgical robot system using a robotic arm of the surgical robot, coupling a reamer to the reamer guide such that a reamer axis passes through the (Continued)

location, constraining movement of the reamer along the reamer axis, and pivoting the reamer at the location to remove bone.

18 Claims, 15 Drawing Sheets

Related U.S. Application Data

(60) Provisional application No. 62/984,038, filed on Mar. 2, 2020.

(51) Int. Cl.
*A61B 34/20* (2016.01)
*A61B 34/30* (2016.01)
*A61B 90/50* (2016.01)

(56) References Cited

U.S. PATENT DOCUMENTS

| | | | |
|---|---|---|---|
| 8,992,542 B2* | 3/2015 | Hagag | A61B 17/1655 606/130 |
| 9,480,580 B2 | 11/2016 | White et al. | |
| 9,561,040 B2 | 2/2017 | Winslow | |
| 9,675,461 B2 | 6/2017 | Mahfouz | |
| 11,801,062 B2 | 10/2023 | Nguyen et al. | |
| 2004/0073226 A1* | 4/2004 | Cotting | A61F 2/34 606/91 |
| 2008/0009874 A1 | 1/2008 | Meridew et al. | |
| 2011/0130761 A1 | 6/2011 | Plaskos et al. | |
| 2017/0312035 A1 | 11/2017 | May et al. | |
| 2018/0325608 A1* | 11/2018 | Kang | A61B 34/20 |
| 2018/0355248 A1* | 12/2018 | Backfolk | A01G 13/0275 |
| 2019/0269467 A1* | 9/2019 | Forsyth | A61B 90/39 |
| 2021/0267609 A1 | 9/2021 | Nguyen et al. | |

FOREIGN PATENT DOCUMENTS

| | | | |
|---|---|---|---|
| WO | WO-2004030555 A1 * | 4/2004 | ............. A61B 34/20 |
| WO | WO-2021174347 A1 | 9/2021 | |

OTHER PUBLICATIONS

"U.S. Appl. No. 17/185,529, Notice of Allowance mailed Jul. 7, 2023", 9 pgs.
"U.S. Appl. No. 17/185,529, Response filed Jan. 30, 2023 to Restriction Requirement mailed Dec. 16, 2022", 8 pgs.
"U.S. Appl. No. 17/185,529, Response filed Apr. 13, 2023 to Non Final Office Action mailed Mar. 16, 2023", 16 pgs.
"U.S. Appl. No. 17/185,529, Restriction Requirement mailed Dec. 16, 2022", 8 pgs.
"Australian Application Serial No. 2021232216, First Examination Report mailed Aug. 10, 2023", 5 pgs.
"Australian Application Serial No. 2021232216, Response filed Sep. 20, 2023 to First Examination Report mailed Aug. 10, 2023", 56 pgs.
"European Application Serial No. 21763523.4, Response to Communication pursuant to Rules 161(2) and 162 EPC filed Apr. 20, 2023", 16 pgs.
"International Application Serial No. PCT/CA2021/050265, International Preliminary Report on Patentability mailed Sep. 15, 2022", 8 pgs.
"International Application Serial No. PCT/CA2021/050265, International Search Report mailed May 12, 2021", 4 pgs.
"International Application Serial No. PCT/CA2021/050265, Written Opinion mailed May 12, 2021", 6 pgs.
U.S. Appl. No. 17/185,529, filed Feb. 25, 2021, Systems and Methods for Co-Operative Control of Robotically-Positioned Surgical Instruments.
"Canadian Application Serial No. 3, 171,358, Examiners Rule 86(2) Report mailed Nov. 30, 2023", 4 pgs.
"Canadian Application Serial No. 3,171,358, Response Filed Mar. 28, 2024 Examiners Rule 86(2) Report mailed Nov. 30, 2023", 26 pgs.
"European Application Serial No. 21763523.4, Extended European Search Report mailed Feb. 26, 2024", 11 pgs.

* cited by examiner

SYSTEMS AND METHODS FOR CO-OPERATIVE CONTROL OF ROBOTICALLY-POSITIONED SURGICAL INSTRUMENTS

CLAIM OF PRIORITY

This application is a divisional of U.S. patent application Ser. No. 17/185,529, filed on Feb. 25, 2021, which claims the benefit of U.S. Provisional Patent Application Ser. No. 62/984,038, filed on Mar. 2, 2020, the benefit of priority of each of which is claimed hereby, and each of which is incorporated by reference herein in its entirety.

TECHNICAL FIELD

The present application pertains generally, but not by way of limitation, to devices and methods for robot-assisted surgical procedures, such as those involving the use of articulating robotic arms that can be moved about multiple axes. More specifically, but not by way of limitation, the present application relates to instrument holders that can be used to position instruments relative to a robotic arm.

BACKGROUND

Imaging of anatomical features can be useful in preparing for and performing surgical procedures. In some surgical procedures it can be desirable to register the shape of the anatomy in the obtained images with another frame of reference, such as the physical space of an operating room. The physical space of the operating room can be correlated to a frame of reference for a robotic surgical system. Robotic surgical arms are used to hold various instruments in place in a desired orientation relative to both the anatomy and operating room during a procedure so that movement of an instrument in the operating room relative to the anatomy can be tracked on the anatomic imaging based on movement of the robotic surgical arm. It is, therefore, desirable to precisely mount instruments to the robotic surgical arm.

Various surgical instruments are described in U.S. Pat. No. 9,561,040 to Winslow, titled "Patient-Specific Glenoid Depth Control"; U.S. Pat. No. 9,480,580 to White et al., titled "Patient-Specific Acetabular Alignment Guides; and Pub. No. US 2008/0009874 to Meridew et al., titled Method and Apparatus for Reaming an Acetabulum.

Overview

The present inventors have recognized, among other things, that problems to be solved with traditional robotic holding devices can include maintaining a surgical instrument in a desired position and orientation with a robotic surgical system while also providing the surgeon with freedom to orient the device into an ergonomic position. During surgeries involving a robotic surgical system, a robotic surgical arm can position an instrument for the surgeon in an orientation suitable to perform the surgical procedure according to a surgical plan. However, the orientation of the instrument may not be in a preferred or comfortable orientation for the surgeon to perform the procedure. As such, the surgeon can suffer discomfort that can aggregate over time into repetitive stress injuries or result in lengthening of the surgical procedure, thereby increasing the cost of the procedure.

The present inventors have also recognized, among other things, that problems to be solved with traditional robotic reaming devices can include difficulty for the surgeon in performing the actual surgical procedure with the instrument while it is held in place by the robotic arm. For example, a reamer shaft can be constrained along a trajectory while being held at the proper depth by the robotic arm. However, constraining of the reamer by the robotic surgical arm can interfere with the ability of the surgeon to freely manipulate the device in a desired manner or pattern to perform the surgical procedure. As such, the surgeon can lose some ability to "feel" the reaming process.

The present subject matter can provide a solution to these and other problems, such as by providing an instrument holder providing collaborative control over an instrument. The collaboratively-controlled instrument can be robotically controlled to constrain movement of the instrument in one or more degrees of freedom, while permitting the surgeon to move the instrument in one or more other degrees of freedom. For example, a robotic arm can macro-position a reamer holder attached to a reamer shaft to control reaming depth and location, which is thereafter constrained by the robotic arm. In other words, the reamer center of rotation can be robotically controlled to ensure surgical accuracy. However, the reamer holder can allow the reamer shaft to be micro-positioned by the surgeon by pivoting the reamer at the reamer center of rotation to allow the reamer shaft to be positioned into a desired orientation and wielded to allow reamer patterning. In other words, the reamer shaft can be oriented to provide surgeon comfort and then moved through a pattern to allow freedom for the surgeon to execute a surgical reaming technique.

The present inventors have also recognized that a problem to be solved is the difficulty of robotic surgical systems to maintain accurate tracking of surgical instruments. It can be relatively easy to track the location of a robotic arm in a surgical space because the robotic arm has a fixed geometry that remains anchored during movement of the surgical arm. Thus, all points on the robotic arm can be tracked back to a known, stationary point in the coordinate system. However, instruments attached to the surgical arm can have different geometries, e.g., lengths, and can be moved relative to the surgical arm during the procedure. Thus, registration techniques for instruments attached to the arm can result in manual adjustments to accommodate differently sized instruments and do not always take into account instruments that move during the surgical procedure.

The present subject matter can provide a solution to these and other problems by providing a dual-registration device for simultaneously registering two reference parameters of an instrument. For example, a reamer shaft can be registered with a first reference parameter defining a center of the reamer shaft axis and with a second reference parameter defining an axis through a known location along the reamer shaft axis. As such, the orientation and location of the reamer shaft can be tracked regardless of different reamer shaft sizes or movement during the surgical procedure.

In an example, a reamer attachment system for attaching a reamer to a robotic arm can comprise a reaming guide comprising a guide shaft and a collar attached to the guide shaft, a reamer shaft extending through the collar and configured to articulate against the collar, and a reamer lock couplable to the reamer shaft to engage the collar and prevent axial displacement of the reamer shaft relative to the collar while permitting the reamer shaft to articulate against the collar.

In an additional example, a robotic surgical system can comprise an articulatable arm configured to move a distal end of the articulatable arm to a location in a coordinate system for the robotic surgical system and a surgical instrument coupler connected to the distal end of the articulatable arm, the surgical instrument coupler comprising a guide shaft extending from the distal end, an articulation coupler connected to the guide shaft at a fixed location relative to the distal end, the articulation coupler defining a pivot center, an instrument shaft connected to the articulation coupler to pivot about the pivot center, and a lock coupled to the instrument shaft to constrain axial movement of the shaft relative to the articulation coupler.

In yet another example, a method for collaborative reaming of a bone socket between a surgical robot and a surgeon can comprise positioning a reamer guide at a location in a coordinate system for the surgical robot system using a robotic arm of the surgical robot, coupling a reamer to the reamer guide such that a reamer axis passes through the location, constraining movement of the reamer along the reamer axis, and pivoting the reamer at the location to remove bone.

In another example, a pointer probe couplable to a quick-coupling device of an instrument shaft can comprise a tracking element, a probe shank extending from the tracking element, the probe shank including a first pointed tip, and a probe extension coupled to the probe shank, the probe extension comprising an elongate shaft for attaching to the quick-coupling device, a first end including a socket for receiving the first pointed tip, and a second end including a second pointed tip.

DETAILED DESCRIPTION

Figure 1:
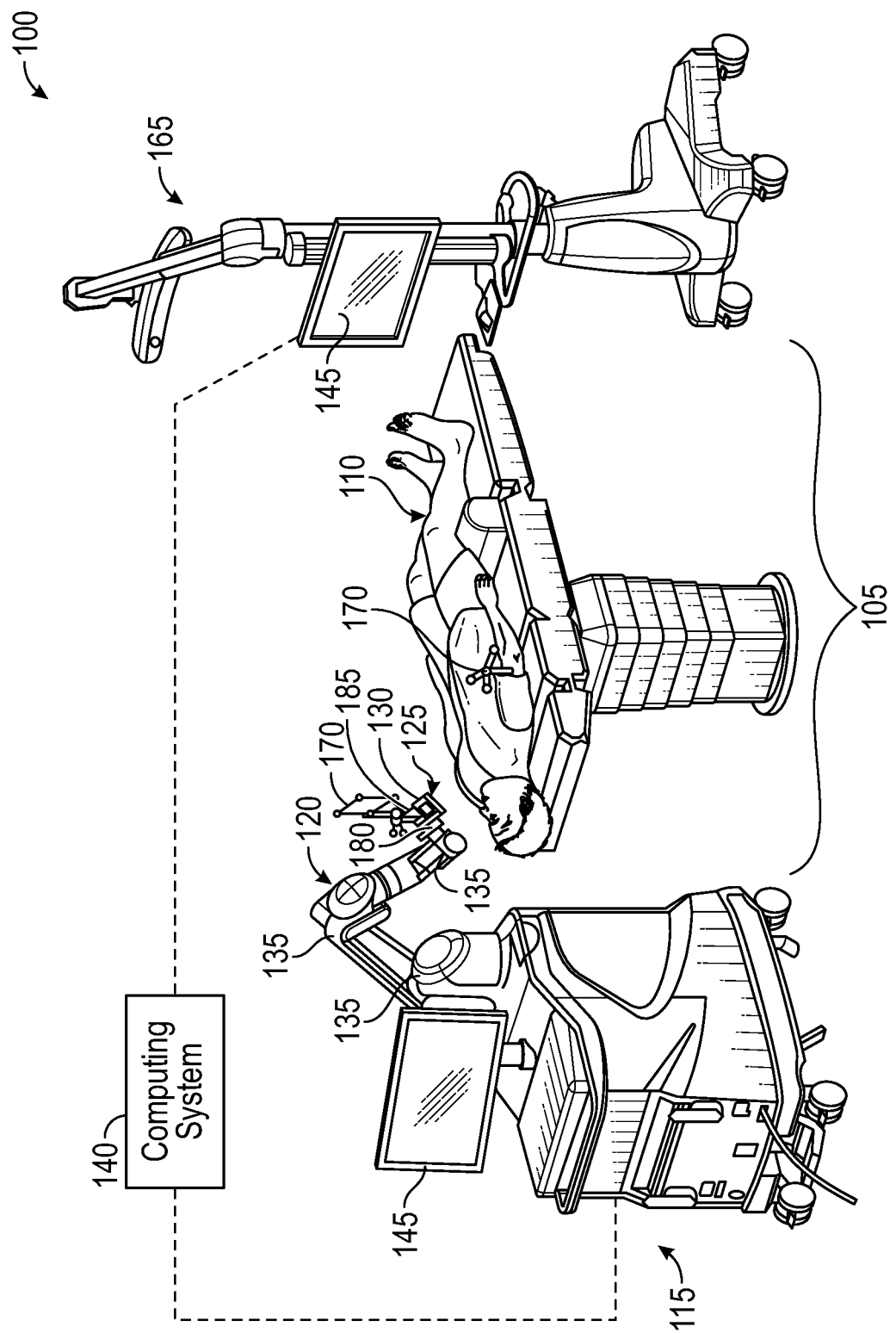
FIG. 1 is a diagrammatic view of an operating room including a robot-assisted surgical system comprising a robotic arm, a computing system and a tracking system.

FIG. 1 illustrates surgical system 100 for operation on surgical area 105 of patient 110 in accordance with at least one example of the present disclosure. Surgical area 105 in one example can include a joint and, in another example, can be a bone. Surgical area 105 can include any surgical area of patient 110, including but not limited to the shoulder, head, elbow, thumb, spine, and the like. Surgical system 100 can also include robotic system 115 with one or more robotic arms, such as robotic arm 120. As illustrated, robotic system 115 can utilize only a single robotic arm. Robotic arm 120 can be a 6 degree-of-freedom (DOF) robot arm, such as the ROSA® robot from Medtech, a Zimmer Biomet Holdings, Inc. company. In some examples, robotic arm 120 is cooperatively controlled with surgeon input on the end effector or surgical instrument, such as surgical instrument 125. In other examples, robotic arm 120 can operate autonomously. While not illustrated in FIG. 1, one or more positionable surgical support arms can be incorporated into surgical system 100 to assist in positioning and stabilizing instruments or anatomy during various procedures.

Each robotic arm 120 can rotate axially and radially and can receive a surgical instrument, or end effector, 125 at distal end 130. Surgical instrument 125 can be any surgical instrument adapted for use by the robotic system 115, including, for example, a guide tube, a holder device, a gripping device such as a pincer grip, a burring device, a reaming device, an impactor device such as a humeral head impactor, a pointer, a probe, a collaborative guide or holder device as described herein or the like. Surgical instrument 125 can be positionable by robotic arm 120, which can include multiple robotic joints, such as joints 135, that allow surgical instrument 125 to be positioned at any desired location adjacent or within a given surgical area 105. As discussed below, robotic arm 120 can be used with a reaming device, e.g., reaming system 200 (FIG. 2), to direct a reamer along a controlled trajectory relative to surgical area 105 based on a virtual coordinate system determined by computing system 140, while still permitting a surgeon to manipulate the reamer within the parameters controlled by robotic arm 120.

Robotic system 115 can also include computing system 140 that can operate robotic arm 120 and surgical instrument 125. Computing system 140 can include at least memory, a processing unit, and user input devices, as will be described herein. Computing system 140 and tracking system 165 can also include human interface devices 145 for providing images for a surgeon to be used during surgery. Computing system 140 is illustrated as a separate standalone system, but in some examples computing system 140 can be integrated into robotic system 115. Human interface devices 145 can provide images, including but not limited to three-dimensional images of bones, glenoid, joints, and the like. Human interface devices 145 can include associated input mechanisms, such as a touch screen, foot pedals, or other input devices compatible with a surgical environment.

Computing system 140 can receive pre-operative, intra-operative and post-operative medical images. These images can be received in any manner and the images can include, but are not limited to, computed tomography (CT) scans, magnetic resonance imaging (MRI), two-dimensional x-rays, three-dimensional x-rays, ultrasound, and the like. These images in one example can be sent via a server as files attached to an email. In another example the images can be stored on an external memory device such as a memory stick and coupled to a USB port of the robotic system to be uploaded into the processing unit. In yet other examples, the images can be accessed over a network by computing system 140 from a remote storage device or service.

After receiving one or more images, computing system 140 can generate one or more virtual models related to surgical area 105. Alternatively, computer system 140 can receive virtual models of the anatomy of the patient prepared remotely. Specifically, a virtual model of the anatomy of patient 110 can be created by defining anatomical points within the image(s) and/or by fitting a statistical anatomical model to the image data. The virtual model, along with virtual representations of implants, can be used for calculations related to the desired location, height, depth, inclination angle, or version angle of an implant, stem, acetabular cup, glenoid cup, surgical instrument, or the like to be utilized in surgical area 105. In another procedure type, the virtual model can be utilized to determine insertion location, trajectory and depth for inserting an instrument. In a specific example, the virtual model can be used to determine a reaming angle relative to an acetabulum of a pelvis and a depth for reaming into the pelvis to place an acetabular implant. The virtual model can also be used to determine bone dimensions, implant dimensions, bone fragment dimensions, bone fragment arrangements, and the like. Any model generated, including three-dimensional models, can be displayed on human interface devices 145 for reference during a surgery or used by robotic system 115 to determine motions, actions, and operations of robotic arm 120 or surgical instrument 125. Known techniques for creating virtual bone models can be utilized, such as those discussed in U.S. Pat. No. 9,675,461, titled "Deformable articulating templates" or U.S. Pat. No. 8,884,618, titled "Method of generating a patient-specific bone shell" both by Mohamed Rashwan Mahfouz, as well as other techniques known in the art.

Computing system 140 can also communicate with tracking system 165 that can be operated by computing system 140 as a stand-alone unit. Surgical system 100 can utilize the Polaris optical tracking system from Northern Digital, Inc. of Waterloo, Ontario, Canada. Additionally, tracking system 165 can comprise the tracking system shown and described in Pub. No. US 2017/0312035, titled "Surgical System Having Assisted Navigation" to Brian M. May, which is hereby incorporated by this reference in its entirety. Tracking system 165 can monitor a plurality of tracking elements, such as tracking elements 170, affixed to objects of interest to track locations of multiple objects within the surgical field. Tracking system 165 can function to create a virtual three-dimensional coordinate system within the surgical field for tracking patient anatomy, surgical instruments, or portions of robotic system 115. Tracking elements 170 can be tracking frames including multiple IR reflective tracking spheres, or similar optically tracked marker devices. In one example, tracking elements 170 can be placed on or adjacent one or more bones of patient 110. In other examples, tracking elements 170 can be placed on robot robotic arm 120, surgical instrument 125, and/or an implant to accurately track positions within the virtual coordinate system associated with surgical system 100. In each instance tracking elements 170 can provide position data, such as patient position, bone position, joint position, robotic arm position, implant position, or the like.

Robotic system 115 can include various additional sensors and guide devices. For example, robotic system 115 can include one or more force sensors, such as force sensor 180. Force sensor 180 can provide additional force data or information to computing system 140 of robotic system 115. Force sensor 180 can be used by a surgeon to cooperatively move robotic arm 120. For example, force sensor 180 can be used to monitor impact or implantation forces during certain operations, such as insertion of an implant stem into a humeral canal. Monitoring forces can assist in preventing negative outcomes through force fitting components. In other examples, force sensor 180 can provide information on soft-tissue tension in the tissues surrounding a target joint. In certain examples, robotic system 115 can also include laser pointer 185 that can generate a laser beam or array that is used for alignment of implants during surgical procedures.

In order to ensure that computing system 140 is moving robotic arm 120 in a known and fixed relationship to surgical area 105 and patient 110, the space of surgical area 105 and patient 110 can be registered to computing system 140 via a registration process involving registering fiducial markers attached to patient 110 with corresponding images of the markers in patient 110 recorded preoperatively or just prior to a surgical procedure. For example, a plurality of fiducial markers can be attached to patient 110, images of patient 110 with the fiducial markers can be taken or obtained and stored within a memory device of computing system 140. Subsequently, patient 110 with the fiducial markers can be moved into, if not already there because of the imaging, surgical area 105 and robotic arm 120 can touch each of the fiducial markers. Engagement of each of the fiducial markers can be cross-referenced with, or registered to, the location of the same fiducial marker in the images. In additional examples, patient 110 and medical images of the patient can be registered in real space using contactless methods, such as by using a laser rangefinder held by robotic arm 120 and a surface matching algorithm that can match the surface of the patient from scanning of the laser rangefinder and the surface of the patient in the medical images. As such, the real-world, three-dimensional geometry of the anatomy attached to the fiducial markers can be correlated to the anatomy in the images and movements of instruments 125 attached to robotic arm 120 based on the images will correspondingly occur in surgical area 105.

Subsequently, other instruments and devices attached to surgical system 100 can be positioned by robotic arm 120 into a known and desired orientation relative to the anatomy. For example, robotic arm 120 can be coupled to a reaming system, such as reaming system 200 of FIG. 2, including a cooperatively positionable reamer of the present disclosure. Robotic arm 120 can move the reamer into a fixed position relative to anatomy of the patient such that an axis of the reamer extends along a desired orientation relative to the anatomy. With robotic arm 120 locked into place, the reaming systems of the present application can limit axial movement of the reamer to control reaming depth. However, the reaming system can also permit the surgeon to engage the reamer in multiple positions and to manipulate the reamer about a reamer pattern without moving off-axis or beyond the desired ream depth.

Figure 2:
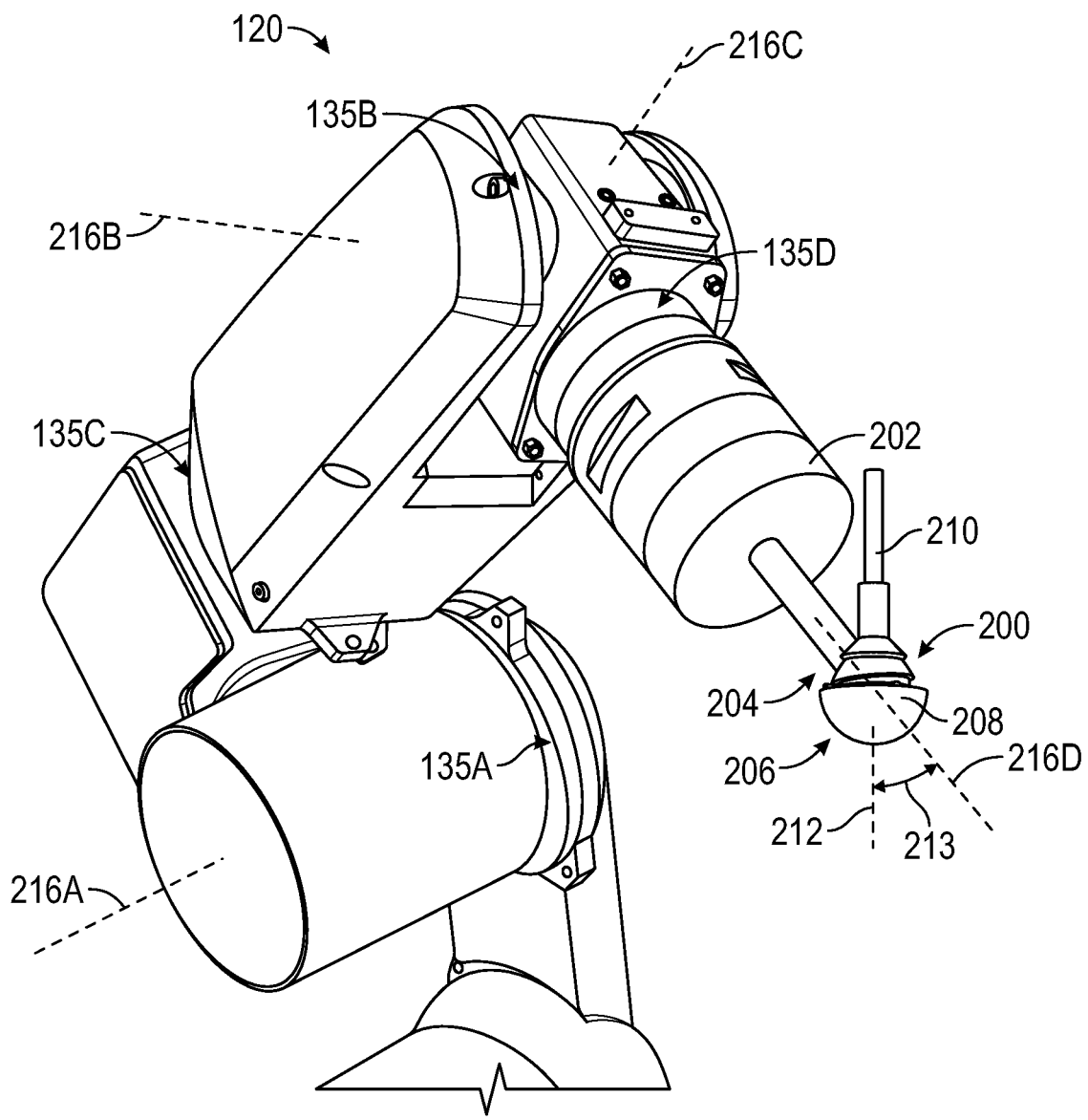
FIG. 2 is a schematic view of the robotic arm of FIG. 1 including a collaboratively-controlled instrument holder configured to robotically support or guide an instrument along an axis while permitting partial surgeon control over the instrument.

FIG. 2 is a schematic view of robotic arm 120 of FIG. 1 including reaming system 200, which can be positioned by robotic arm 120 relative to surgical area 105 (FIG. 1) in a desired orientation according to a surgical plan, such as a plan based on preoperative imaging. Reaming system 200 can comprise tool base 202, reaming guide 204 and reamer 206. Reamer 206 can comprise reamer head 208 and reamer shaft 210, which can extend along axis 212.

Robotic arm 120 can include joint 135A that permits rotation about axis 216A, joint 135B that can permit rotation about axis 216B, joint 135C that can permit rotation about axis 216C and joint 135D that can permit rotation about axis 216D. Reaming guide 204 can extend along a guide axis that can be coincident with axis 216D for joint 135D. Reamer axis 212 can be positioned at angle 213 relative to axis 216D via reaming guide 204. In examples, angle 213 can be in a range of approximately five degrees to approximately twenty-five degrees.

In order to position reaming system 200 relative to anatomy of patient 110 (FIG. 1), surgical system 100 (FIG. 1) can manipulate robotic arm 120 automatically by computing system 140 or a surgeon manually operating computing system 140 to move reaming system 200 to the desired location, e.g., a location called for by a surgical plan to align an instrument relative to the anatomy. For example, robotic arm 120 can be manipulated along axes 216A-216D to position reaming guide 204 such that reamer head 208 is located in a reaming location. With robotic arm 120 being immobilized (e.g., not moving) or locked in place, reaming guide 204 can position the center of reaming head 208 along a planned surgical trajectory and limit axial movement of reaming head beyond a planned surgical depth. However, reaming guide 204 can allow for tilting of reamer shaft 210 such that reamer head 208 can pivot about a center point to enable a surgeon to operate reamer 206 in an ergonomic manner and to move reamer head 208 in multiple, different passes across a bone surface to, for example, allow the surgeon to eliminate cutting tooth tracks in the bone surface. Thus, reamer shaft 210 can be moved to vary angle 213 relative to axis 216D.

Figure 13:
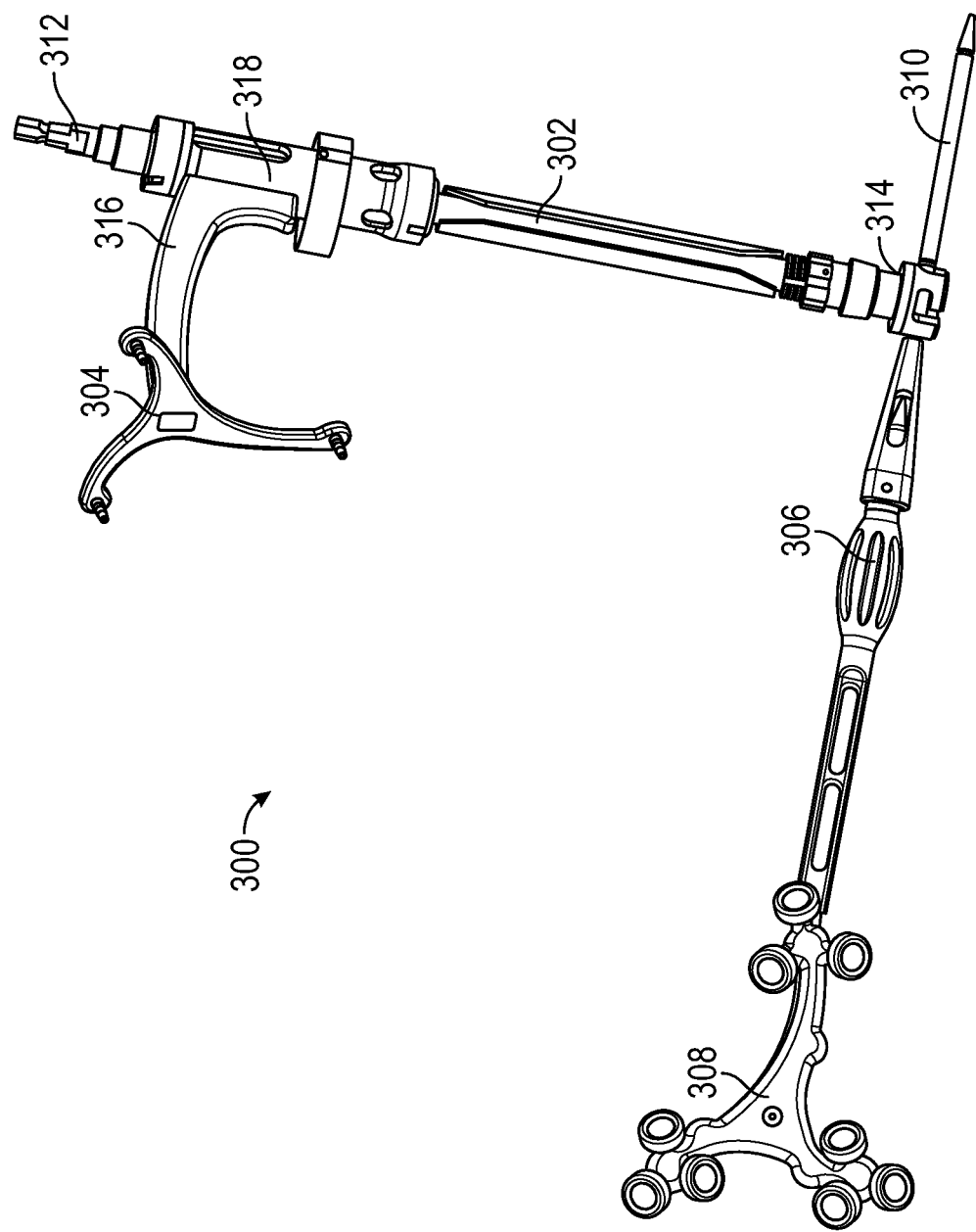
FIG. 13 is a perspective view of a registration system for a reaming system of the present disclosure showing a reamer shaft, a reamer tracker, a registration pointer, a pointer tracker and a pointer extension.

Robotic arm 120 can be separately registered to the coordinate system of surgical system 100, such via use of a tracking element 170 (FIG. 1). Fiducial markers can additionally be separately registered to the coordinate system of surgical system 100 via engagement with a probe having a tracking element 170 attached thereto. Reaming guide 204 and reamer 206 can be registered to the coordinate system using trackers 304 and 308 (FIG. 13). As such, some or all of the components of surgical system 100 can be individually registered to the coordinate system and, if desired, movement of such components can be continuously or intermittently tracked with a tracking element 170.

It can be a difficult task to ensure instruments attached to robotic arm 120 are accurately aligned with and positioned relative to patient 110, particularly if instruments come in different sizes or the instrument needs to be individually manipulated during the procedure, such as by intervention of personnel including a surgeon. For example, sometimes robotic arm 120 is positioned to provide the proper alignment of an instrument, e.g., a reamer shaft or guide pin, that needs to be inserted into the patient. Thus, robotic arm 120 can automatically provide a trajectory for an instrument, while the surgeon manually provides the motive force for the instrument, e.g., rotation for a reamer shaft and insertion force for a guide pin. However, once the surgeon moves the instrument relative to robotic arm 120, the precise location of the instrument, e.g., the location of the tip of the instrument in the coordinate system, can become lost or obfuscated, and surgical system 100 will not be able to reproduce the location of said tip in imaging of the patient.

In some robotic procedures instruments can be separately tracked using an optical navigation system that, under ideal conditions, alleviate the need for precisely maintaining axis 212 and the location of an instrument along axis 212 through a surgical procedure or surgical task, as the optical navigation system can provide the surgical computer system information to compensate for any changes. However, as optical navigation systems require line-of-sight with the instruments to be maintained, there is a significant advantage in not requiring instruments to be navigated (or at least not constantly navigated). Accordingly, the ability to precisely maintain orientation of axis 212 and position along axis 212 provides the additional advantage of at least reducing, and possibly eliminating, the need to navigate instruments during a robotic procedure.

In order to improve the ability to determine the location of instruments within the coordinate system, such as along axis 212, the present application describes, with reference to FIGS. 13-16, a registration device configured to provide two reference points on an instrument during a registration procedure to allow for orientation and depth tracking of the instrument. Thus, a trajectory or orientation of a reaming axis can be determined, as well as a reaming point along the reaming axis to ensure that a specific reamer shaft does not move beyond a planned surgical depth. After the registration process, the reaming axis orientation and reaming point can be continuously monitored via coupling to robotic arm 120 without requiring line-of-sight or specialty instruments, such that the position of the instrument relative to robotic arm 120 and the coordinate system can be determined.

Figure 3:
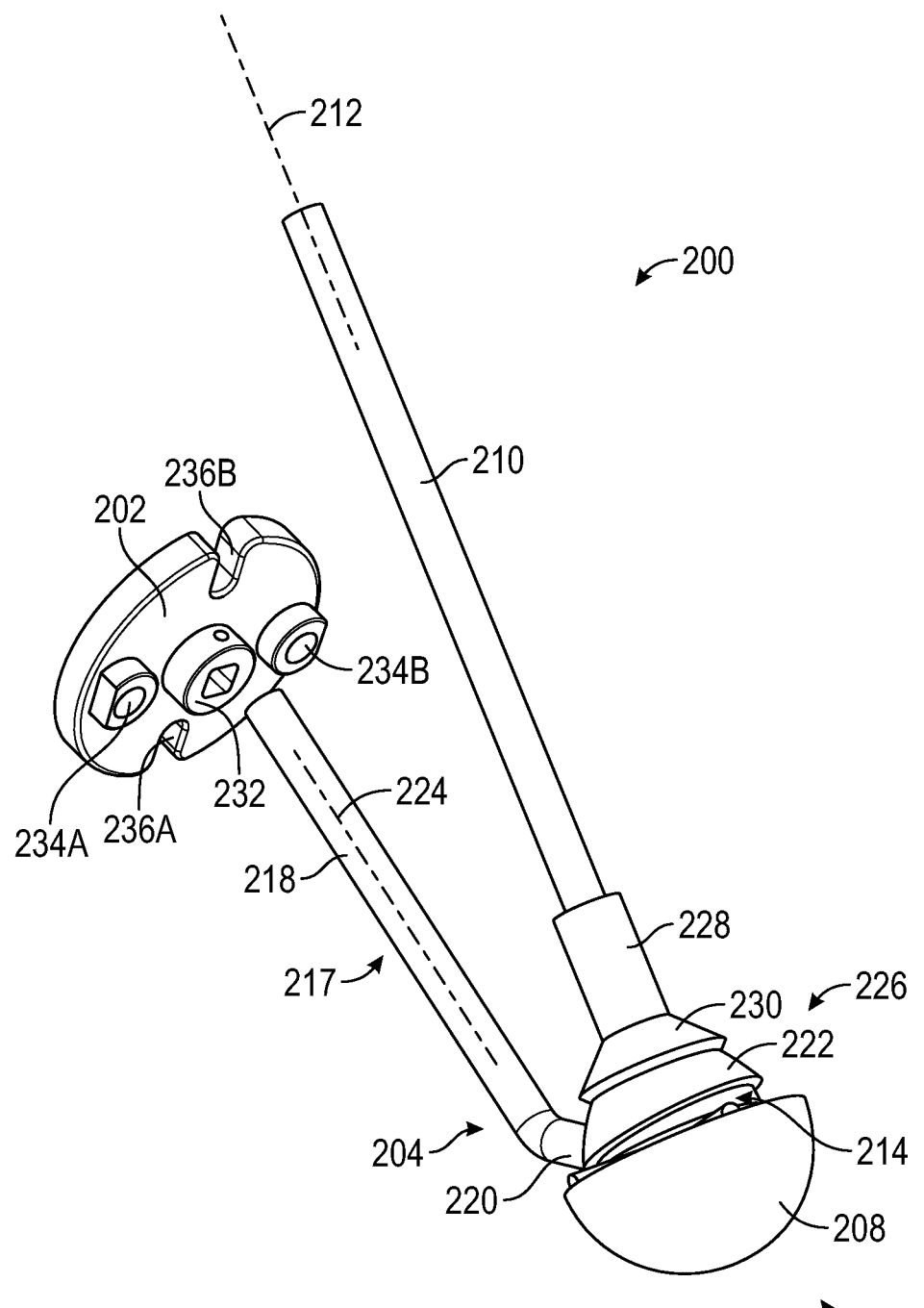
FIG. 3 is a perspective view of a reaming system of the present disclosure that provides collaborative surgeon and robot control of a reamer.
Figure 4:
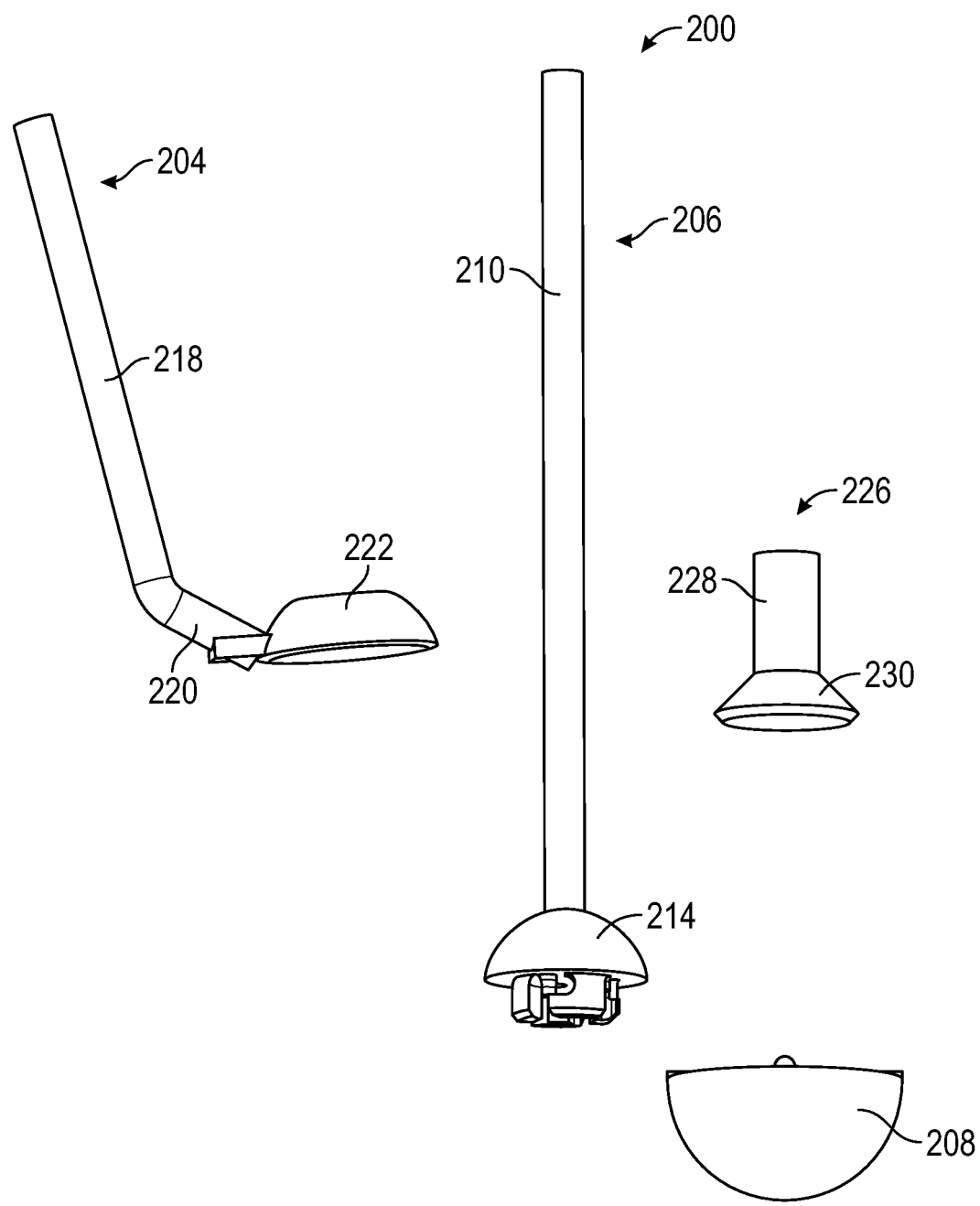
FIG. 4 is an exploded view of the reaming system of FIG. 3 showing a reaming guide, a reamer shaft, a reamer head and a reamer lock.

FIG. 3 is a perspective view of reaming system 200 of the present disclosure that provides collaborative surgeon and robot control of a reamer 206 using reaming guide 204. FIG. 4 is an exploded view of reaming system 200 of FIG. 3 showing reaming guide 204, reamer shaft 210, reamer head 208 and reamer lock 226. FIGS. 3 and 4 are discussed concurrently.

Reamer 206 can comprise reamer head 208, reamer shaft 210 and coupler 214. Reaming guide 204 can comprise guide shaft 217, which can comprise main shaft 218 and attachment shaft 220, and collar 222. Main shaft 218 can extend along guide axis 224, which is configured to be coaxial with axis 216D (FIG. 2). Reaming system 200 can further comprise lock 226. Lock 226 can comprise tubular body 228 and flared portion 230. Tool base 202 (FIG. 3) can comprise collar 232, mounting bores 234A and 234B and slots 236A and 236B.

Tool base 202 can be coupled to robotic arm 120 by inserting fasteners through mounting bores 234A and 234B and into mating bores in robotic arm 120. Slots 236A and 236B can be receive alignment features on robotic arm 120 to ensure proper mounting of tool base 202. Main shaft 218 of reamer shaft 210 can be inserted into collar 232 and secured therein by any suitable means, such as a threaded coupling, locking pins or a combination thereof. Main shaft 218 can extend along guide axis 224 that can be coaxial with axis 216D (FIG. 2) of robotic arm 120. Attachment shaft 220 can extend from main shaft 218 to position collar 222 away from axis 224. Reamer shaft 210 can extend through collar 222 to position coupler 214 within collar 222. Lock 226 can be positioned about reamer shaft 210 to engage collar 222. Reamer head 208 can be attached to coupler 214 of reamer 206.

Assembled as such, reamer shaft 210 can be articulated by a user, such as a surgeon, to pivot coupler 214 within collar 222, while guide shaft 217 can hold collar 22 in a fixed position to thereby constrain the center of reamer head 208 with the aid of lock 226. Thus, robotic arm 120 (FIG. 2) can be used to position reamer head 208 at the desired orientation and depth relative to a patient and the surgeon can position reamer shaft 210 in an ergonomic position and can move reamer shaft 210 through a reaming pattern to ensure adequate and smooth reaming of the reamed surface, e.g., bone surface.

Figure 5:
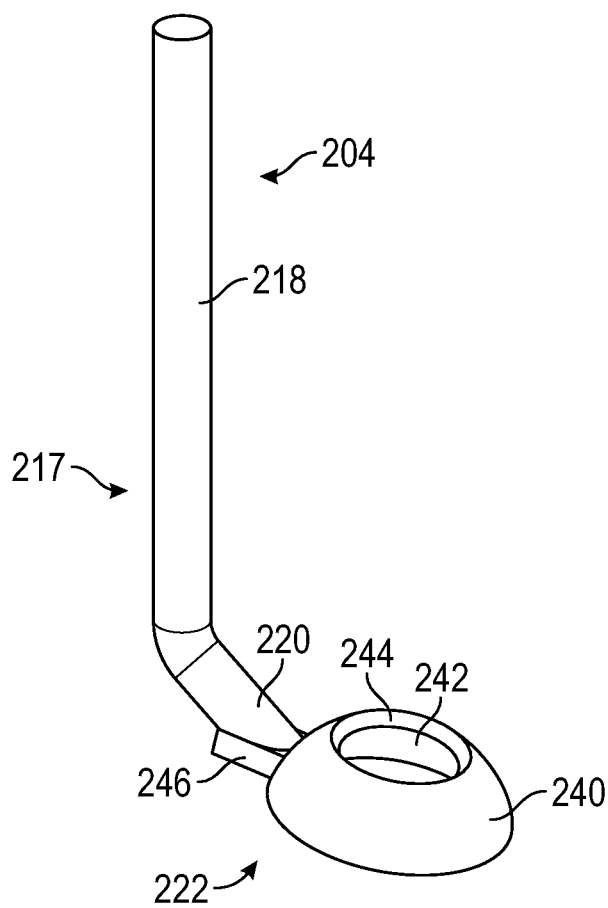
FIG. 5 is a perspective view of the reaming guide of FIG. 4.
Figure 6:
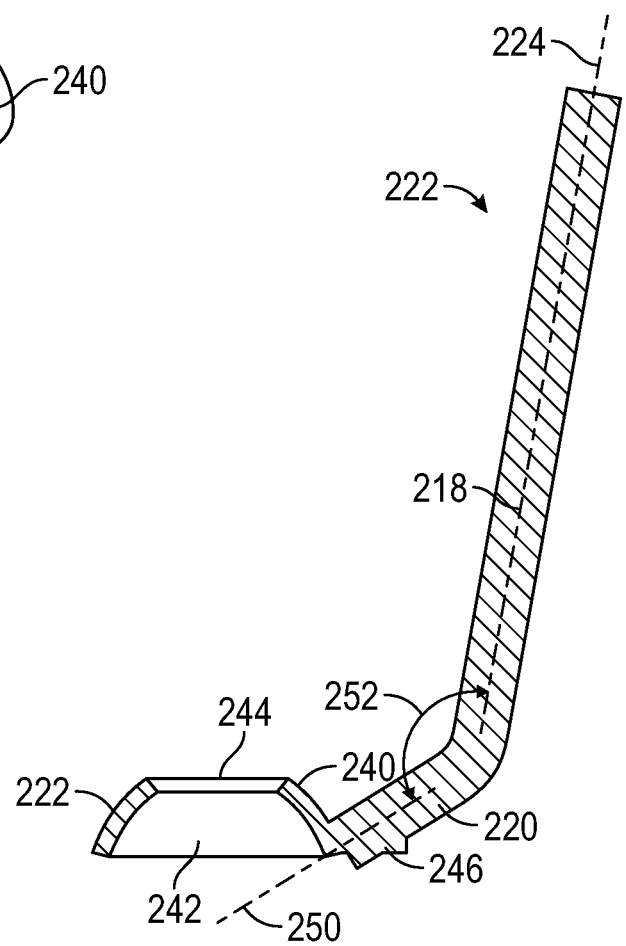
FIG. 6 is a cross-sectional view of the reaming guide of FIG. 5.

FIG. 5 is a perspective view of reaming guide 204 of FIG. 4. FIG. 6 is a cross-sectional view of reaming guide 204 of FIG. 5. FIGS. 5 and 6 are discussed concurrently.

Reaming guide 216 can comprise guide shaft 217, which can comprise main shaft 218 and attachment shaft 220, and collar 222. Collar 222 can comprise outer surface 240, inner surface 242 and aperture 244 extending therebetween from a proximal end to a distal end. Guide shaft 217 can further comprise flange 246 to facilitate attachment of attachment shaft 220 to collar 222.

Attachment shaft 220 can extend along extension axis 250. Extension axis 250 can be positioned relative to guide axis 224 at angle 252. The length of attachment shaft 220 and the magnitude of angle 252 can be set to offset collar 222 from guide axis 224, and can be selected based on ergonomic considerations for positioning of reamer 206. Outer surface 240 and inner surface 242 can be smooth and curve to provide surfaces against which lock 226 and coupler 214 can articulate, respectively. In examples, outer surface 240 and inner surface 242 can comprises sections of spheres.

Figure 7:
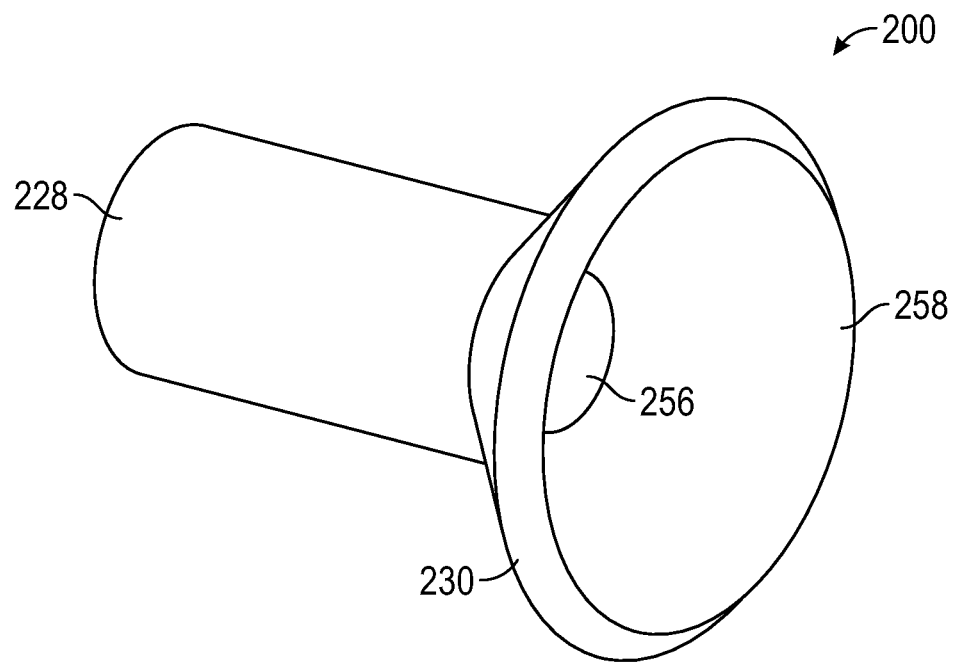
FIG. 7 is a perspective view of the reamer lock of FIG. 4.
Figure 8:
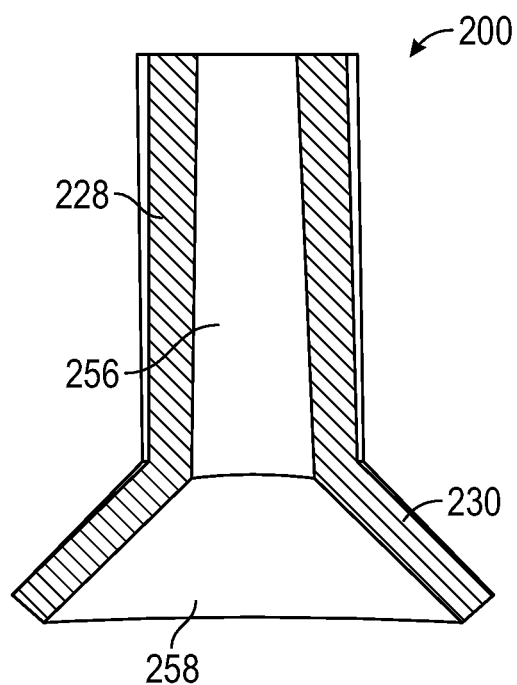
FIG. 8 is a cross-sectional view of the reamer lock of FIG. 7.

FIG. 7 is a perspective view of reamer lock 226 of FIG. 4. FIG. 8 is a cross-sectional view of reamer lock 226 of FIG. 7. FIGS. 7 and 8 are discussed concurrently.

Reamer lock 226 can comprise tubular body 228 and flared portion 230. Tubular body 228 can comprise channel 256 and flared portion 230 can comprise articular surface 258. In an example, reamer lock 226 can be fabricated from a polymeric material to facilitate frictional engagement with reamer shaft 210, which can be made of a metal such as stainless steel, and to allow for a degree of deformability to receive reamer shaft 210.

Tubular body 228 can comprise an elongate member for sliding against reamer shaft 210 (FIGS. 3 and 4.) Channel 256 can be sized to closely conform to the outer perimeter size of reamer shaft 210. In an example, channel 256 can have a diameter slightly larger than the diameter of reamer shaft 210 to provide a frictional engagement. The frictional engagement can be strong enough to hold lock 226 in place against reamer shaft 210 such that pushing of reamer 206 distally (e.g., down with reference to FIG. 3) does not cause lock 226 to slide upward along reamer shaft 210.

Figure 12:
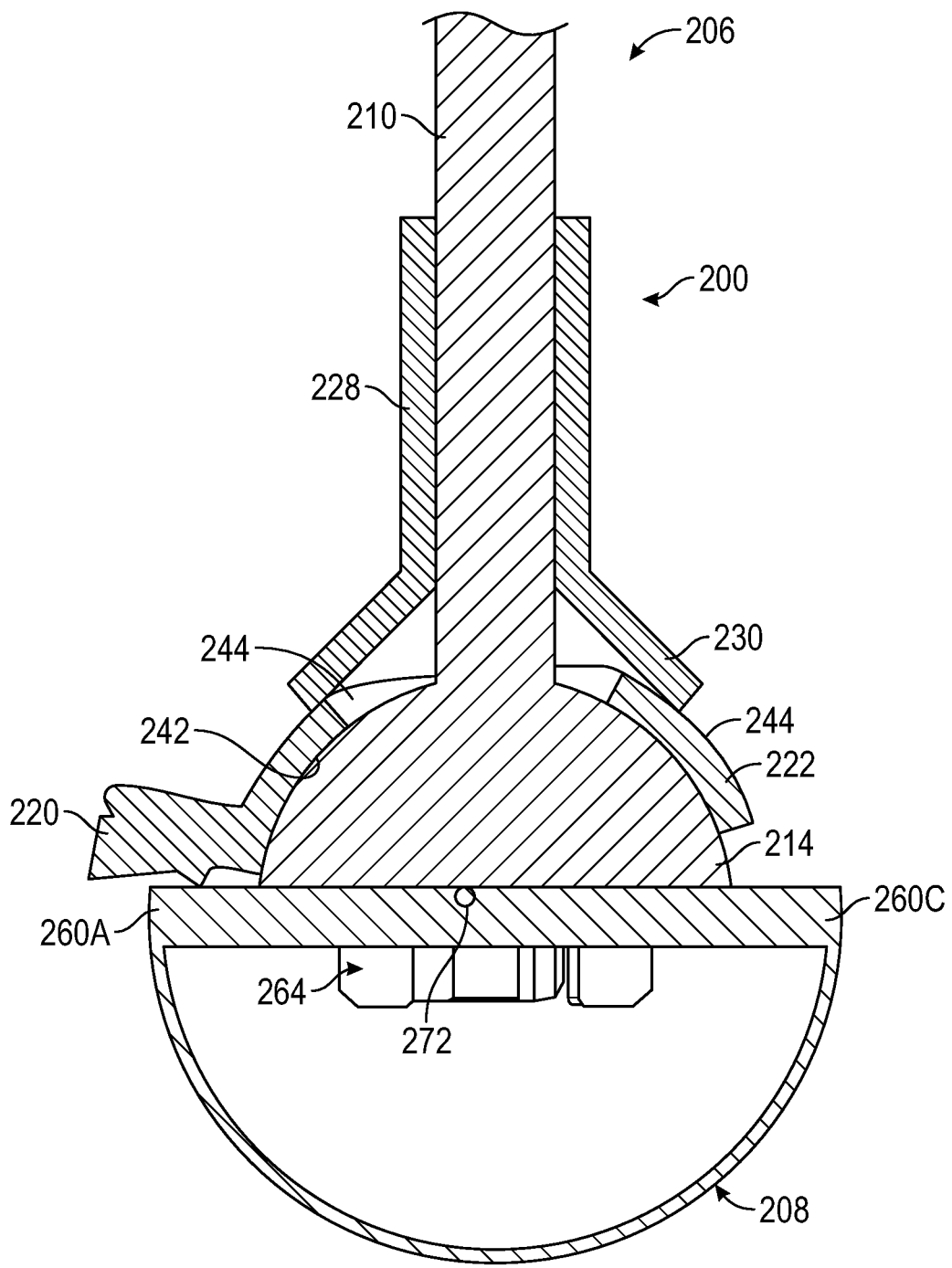
FIG. 12 is a cross-sectional view of the reaming system of FIGS. 3 and 4 showing engagement of articulation surfaces.

Flared portion 230 can comprise a body configured to engage collar 222. In an example, flared portion 230 can comprise a conical body extending from the distal end of tubular body 228. Flared portion 230 can enlarge the diameter of tubular body 228 to increase the surface area engagement with collar 222. Furthermore, as can be seen in FIG. 12, for example, flared portion 230 can extend to a diameter larger than aperture 244 in collar 222.

Figure 9:
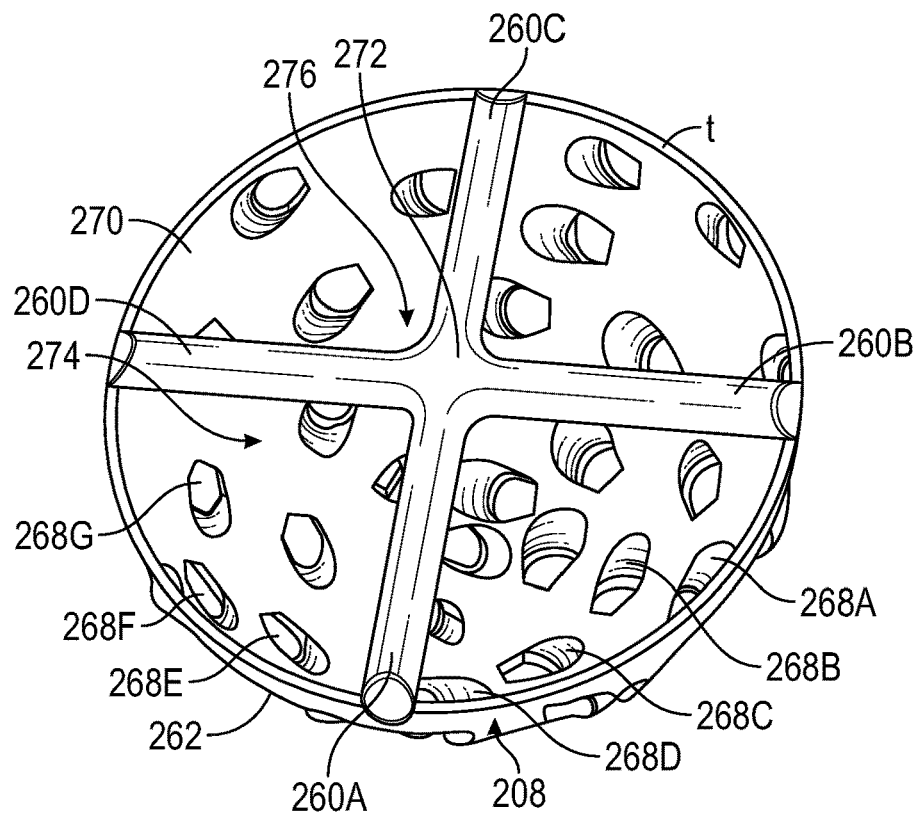
FIG. 9 is a perspective view of a rear side of the reamer head of FIG. 4 showing attachment members.
Figure 10:
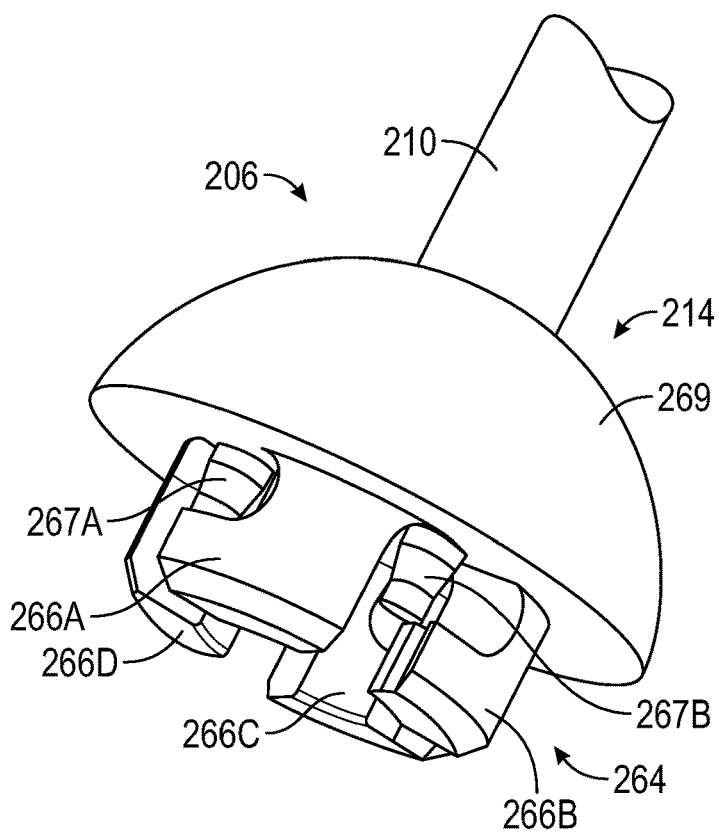
FIG. 10 is a perspective view a distal end of the reamer shaft of FIG. 4 showing a quick-coupling device.
Figure 11:
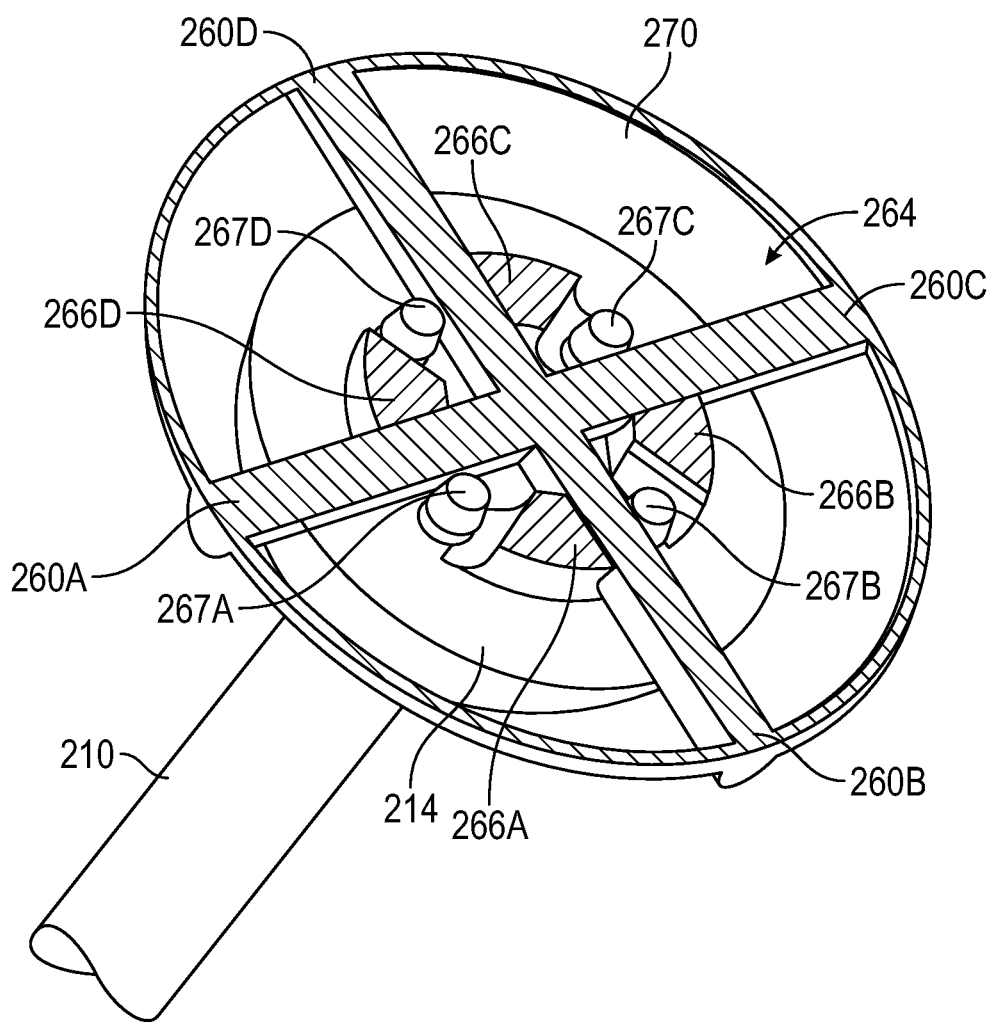
FIG. 11 is a cross-sectional view of the reamer head and reamer shaft of FIGS. 9 and 10 coupled via engagement of the quick-coupling device with the attachment members.

FIG. 9 is a perspective view of a rear side of reamer head 208 of FIG. 4 showing attachment members 260A-260D, reaming surface 262 and inner surface 270. FIG. 10 is a perspective view a distal end of reamer shaft 210 of FIG. 4 showing quick-coupling device 264. Quick-coupling device 264 can comprise a bayonet coupler including receptors 266A-266D and detents 267A-267D. FIG. 11 is a cross-sectional view of reamer head 208 and reamer shaft 210 of FIGS. 9 and 10 coupled via engagement of quick-coupling device 264 with attachment members 260A-260D. FIGS. 9-11 are discussed concurrently.

Reamer head 208 can comprise a device for removing bone. As such, reamer head 208 can comprise cutting elements 268A-268G. Cutting elements 268A-268G are labeled for illustrative purposes, but reamer head 208 can include any number of cutting elements. Reamer head 208 can include any shape or style of cutting elements suitable for cutting bone as is known in the art, such as scallops.

Reamer head 208 can comprise a shell having reaming surface 262 and inner surface 270. Reaming surface 262 can be hemispherical in shape such that all points on surface 262 are approximately equidistant from center point 272 of the hemisphere. Inner surface 270 can also be hemispherical in shape such that the shell of reamer head 208 has a uniform shape. Thus, the shell of reamer head 208 can have a uniform or nearly uniform thickness t. Inner surface 270 can form interior space 274. Cutting elements 268A-268G can comprise scallops or teeth that penetrate into interior space 274. As such, cutting elements 268 can comprise openings in reamer head 208 with raised edges that are sharpened. Thus, material, e.g., bone, removed by cutting elements 268A-268G can pass into interior space 274 and out of reamer head 208 during a reaming operation.

Attachment members 260A-260D can comprise rods or bars extending across interior space 274. Attachment members 260A-260D can intersect at intersection 276, which can be located at center point 272.

Reamer head 208 can comprise a part that can be interchangeable with reamer shaft 210. As such, different reamer heads can be attached to reamer shaft 210, such as intraoperatively (e.g., within the same surgery) to achieve different reaming effects or inter-operatively (e.g., between different surgeries) for cleaning, maintenance (e.g., sharpening) if the cutting elements become dull, or disposal.

Coupler 214 can comprise articulating surface 269 and quick-coupling device 264. Articulating surface 269 can comprise a curved surface for abutting inner surface 242 (FIG. 5). In examples, inner surface 242 and articulating surface 269 can comprise spherical surfaces.

Quick-coupling device 264 can comprise a device configured to connect to attachment members 260A-260D of reamer head 208. Receptors 266A-266D can comprise slots configured to receive attachment members 260A-260D. Detents 267A-267D can comprise spring-loaded pins biased away from reamer shaft 210 and toward receptors 266A-266D. As such, detents 267A-267D can press against attachment members 260A-260D, respectively, to immobilize reamer head 208 relative to reamer shaft 210. In an example, reamer head 208 and quick-coupling device 264 can comprise components described in U.S. Pat. No. 9,480,580 to White et al. and titled "Patient-Specific Acetabular Alignment Guides," the contents of which are incorporated in their entirety by this reference.

FIG. 12 is a cross-sectional view of reaming system 200 of FIGS. 3 and 4. As discussed, reamer head 208 can be attached to coupler 214 of reamer 206 via quick-coupling device 264, reamer shaft 210 can be inserted through aperture 244 of collar 222 on reaming guide 204 such that articulating surface 269 (FIG. 10) abuts inner surface 242 of collar 222, and reamer lock 226 can be positioned around reamer shaft 210 such that flared portion 230 engages outer surface 240 of collar 222.

Tubular body 228 of reamer lock 226 can frictionally engage reamer shaft 210 to prevent reamer lock 226 from sliding (upwardly with reference to FIG. 12) along reamer shaft 210 out of engagement with collar 222. As such, reamer lock 226 can pinch collar 222 between flared portion 230 and coupler 214. Thus, reamer shaft 210 is prevented from passing further into collar 222 such that center point 272 is immobilized relative to reaming guide 204. However, aperture 244 can be larger than the diameter of reamer shaft 210, but smaller than the diameter of coupler 214, to allow reamer shaft 210 to be pivoted about center point 272. Thus, reamer shaft 210 can be moved to cause articular surface 269 to slide against inner surface 242 and flared portion 230 to slide against outer surface 240. Thus, reamer 206 can be constrained in axial movement by reaming guide 204, but reaming guide 204 can provide a articulatable coupler that allows shaft 210 to be pivoted at center point 272. Such functionality provides collaborative robotic and surgeon control of reamer 206 to ensure adherence to a surgical plan while providing flexibility for surgeon preference of orientation and technique.

FIG. 13 is a perspective view of registration system 300 for reaming system 200 of the present disclosure showing reamer shaft 302, reamer tracker 304, registration pointer 306, pointer tracker 308 and pointer extension 310.

Reamer shaft 302 can comprise a device for coupling a reamer head to a drive input. A proximal end of reamer shaft 302 can comprise drive lock 312 configured to receive a rotational input from a rotary drive mechanism, such as a handheld, powered drill. A distal end of reamer shaft 302 can comprise quick-coupling device 314. Quick-coupling device 314 can be configured similarly as quick-coupling device 264 of FIG. 10. Reamer shaft 302 can be configured similarly as reamer shaft 206 of FIG. 10.

Reamer tracker 304 can comprise an input device for surgical system 100. In particular, reamer tracker 304 can comprise a tracking array, such as tracking element 170 of FIG. 1, that can provide location information to robotic system 115. Reamer tracker 304 can be coupled to reamer shaft 302 via arm 316. Arm 316 can attach reamer tracker 304 to reamer shaft 302 at a fixed location. For example, reamer tracker 304 can be attached to reamer shaft 302 via sleeve 318. As such, reamer tracker 304 can inform surgical system 100 (FIG. 1) of the location of reamer shaft 302. For example, reamer tracker 304 can inform surgical system 100 of the location of the central axis of reamer shaft 302, e.g., reamer axis 212 of FIG. 3, within the coordinate system of robotic system 115. Reamer tracker 304 can be removable from reamer shaft 302 to facilitate use with other instruments and cleaning and sterilization of reamer shaft 302. As such, since not all reamer shafts are the same length and sleeve 318 may not couple to the reamer shaft 302 in the exact same location every time, the exact location of quick-coupling device 314 can sometimes not be accurately known by robotic system 115. Thus, pointer tracker 308 can be attached to reamer shaft 302 using pointer extension 310 to locate the distal end of reamer shaft 302.

Figure 14:
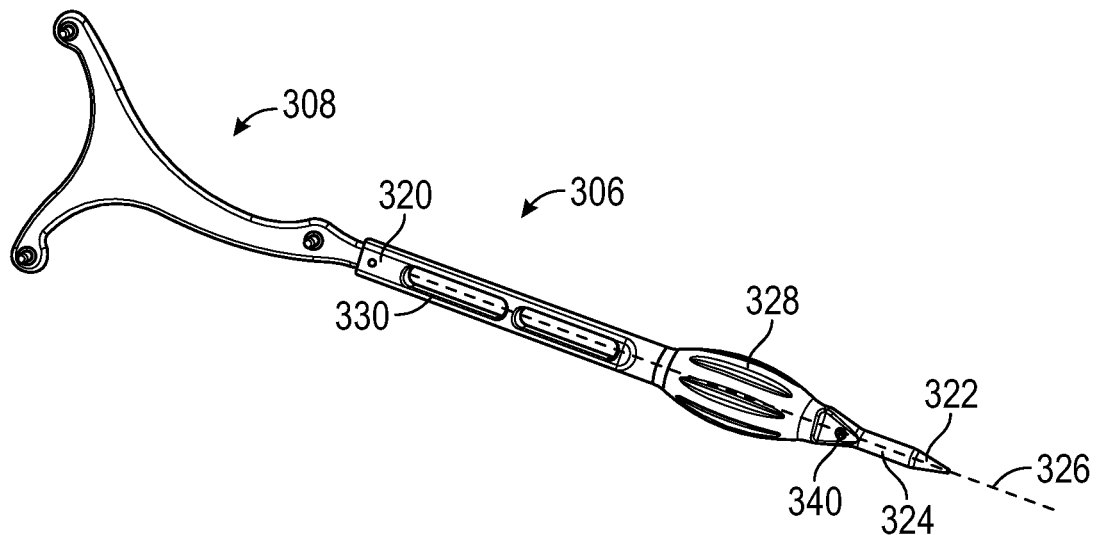
FIG. 14 is a perspective view of the registration pointer and pointer tracker of FIG. 13.

FIG. 14 is a perspective view of registration pointer 306 and pointer tracker 308 of FIG. 13. Registration pointer 306 can comprise a device for contacting specific locations in the coordinate system of robotic system 115 using pointer tracker 308. Pointer tracker 308 can comprise a tracking array, such as tracking element 170 of FIG. 1, that can provide location information to robotic system 115. Pointer tracker 308 can be inserted into socket 320 and secured thereto by a pin or the like to fix the location of pointer tracker 308 relative to tip 322. Tip 322 can comprise a pointed end of shaft 324 that can be used to engage tissue of a patient to mark locations for the coordinate system of robotic system 115. Tip 322 can be pressed into bone, for example, while pointer tracker 308 provides a reading to surgical system 100. Thus, pointer tracker 308 can provide an indication of the location of pointer axis 326 to robotic system 115. Registration pointer 306 can further comprise handle 328. Handle 328 can provide an ergonomic grip for registration pointer 306 to allow manipulation by a surgeon. In order to increase the accuracy of the registration process, it is desirable for pointer shank 330 to extend over a length to increase the location reading of axis 326 taken at tip 322. It is also desirable for handle 328 to be located close to tip 322 to allow a surgeon to easily place tip 322 where desired.

Figure 15:
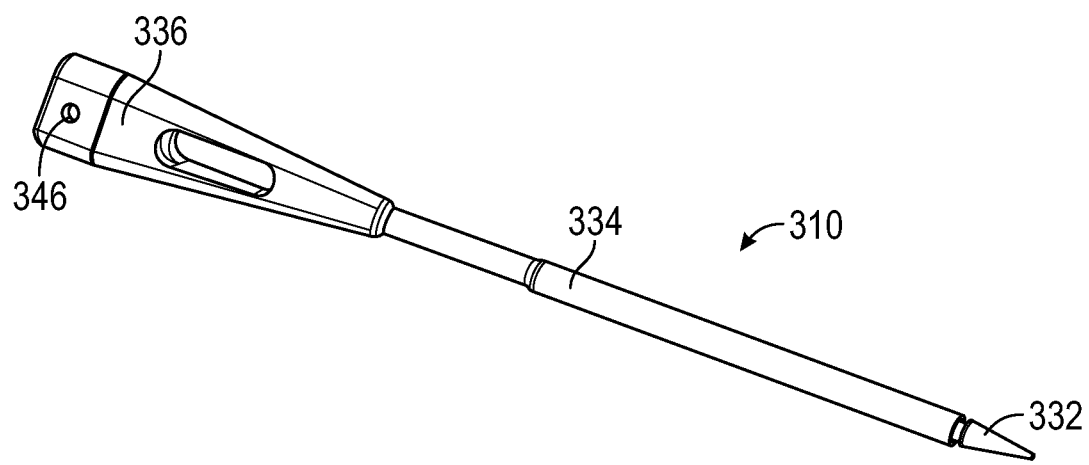
FIG. 15 is a perspective view of the pointer extension of FIG. 13.

FIG. 15 is a perspective view of pointer extension 310 of FIG. 13. Pointer extension 310 can comprise tip 332, shaft 334 and coupler 336. Pointer extension 310 can comprise a device that allows registrations of positions in hard to reach locations. For example, shaft 334 can provide an extension of shaft 324 of registration pointer 306 of FIG. 14. Because pointer tracker 308 can be used to find the location of axis 326, the total length between tip 322 and pointer tracker 306 can change while still providing accurate location information. Coupler 336 allows tip 322 of pointer tracker 308 to couple to pointer extension 310. Coupler 336 can join pointer tracker 308 and pointer extension 310 such that shaft 334 and shaft 324 are coaxial. That is, axis 326 of registration pointer 306 can extend through the center of shaft 324 to tip 322. As such, shaft 334 provides a lengthy body for allowing insertion of tip 332 deep into tissue. Additionally, shaft 334 allows for pointer extension 310, as well as pointer tracker 308 via coupling with registration pointer 306, to be joined to reamer shaft 302 (FIG. 13) or reamer shaft 210 (FIG. 4) via quick-coupling device 314. As such, shaft 334 is sufficiently long to facilitate engagement with opposing receptors 266A-266D of quick-coupling device 264, for example.

Figure 16:
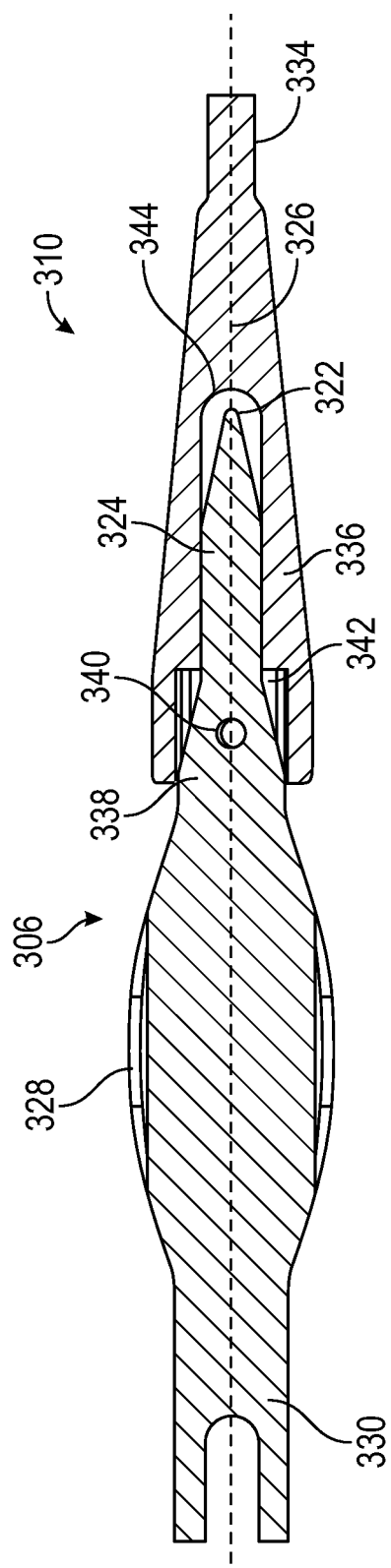
FIG. 16 is a cross-sectional view of the registration pointer inserted into the pointer extension.

FIG. 16 is a cross-sectional view of registration pointer 306 inserted into pointer extension 310. Registration pointer 306 can comprise shaft 324, axis 326, handle 328, shank 330, shoulder 338 and bore 340. Pointer extension 310 can comprise shaft 334, coupler 336, socket 342, window 344 and bore 346 (FIG. 15). Shaft 334 can be inserted into window 344. Window 334 can have a height that closely matches the diameter of shaft 334 to, for example, provide a force fit. Window 334 can be open laterally to allow viewing of tip 322 within window 334. Shoulder 338 can engage socket 342 to prevent rotation of registration pointer 306 relative to axis 326. A pin can be placed through bore 340 and bore 346 (FIG. 15) to fasten registration pointer 306 to pointer extension 310. Engagement of shoulder 338 and shaft 324 with socket 342 and window 334 can also ensure alignment of shaft 334 with axis 326 of shank 330, thereby allowing pointer extension 310 to function as an accurate longitudinal extension of registration pointer 306.

Figure 17:
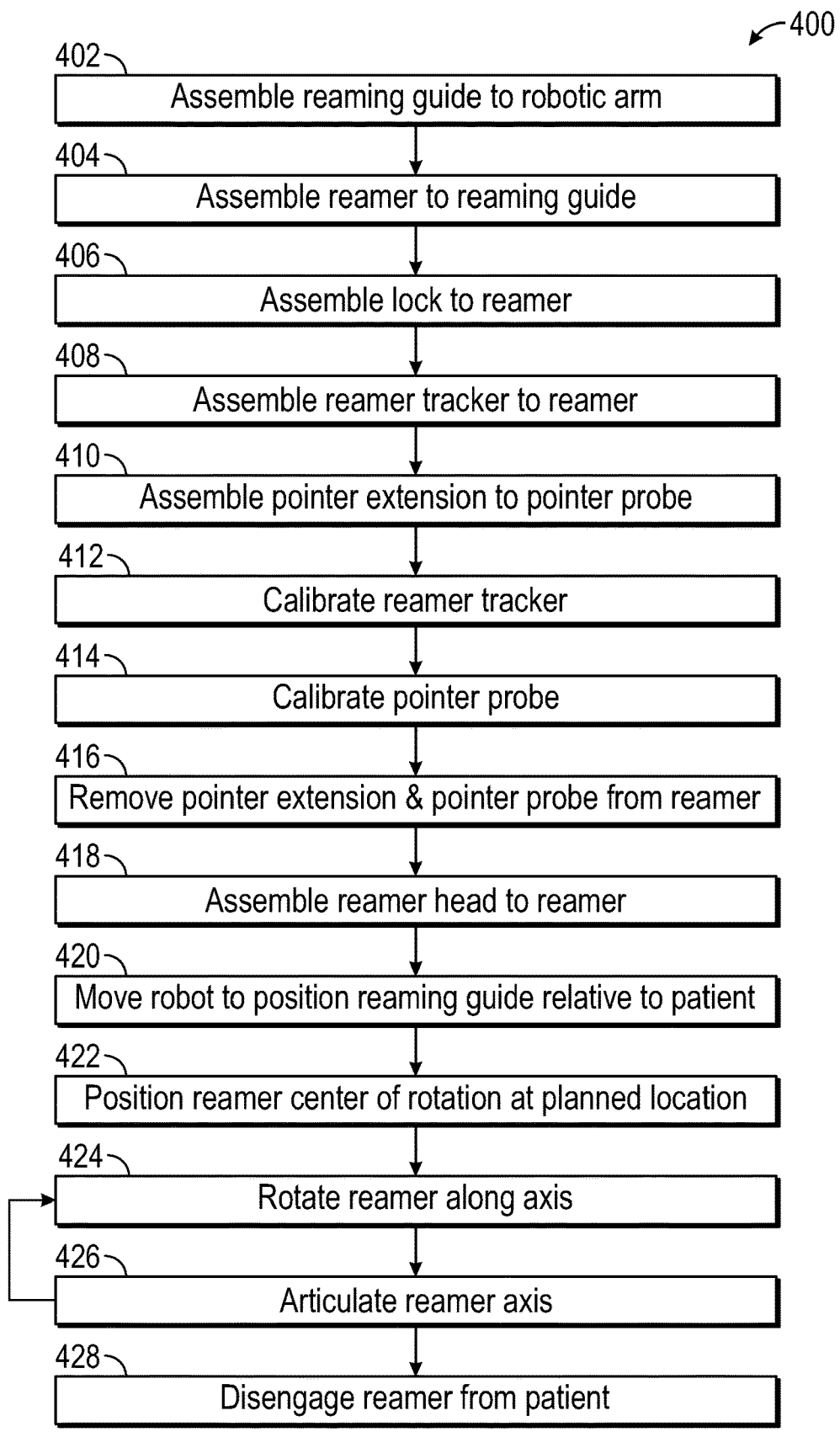
FIG. 17 is a flow chart illustrating steps of methods for assembling an instrument holder with a reaming device and a robotic surgical system, calibrating the reaming device in the instrument holder and using the instrument holder with the reaming device.

FIG. 17 is a flow chart of method 400 illustrating steps 402-428 of methods for assembling a collaborative instrument guide holder for use with a robotic surgical system and calibrating an instrument coupled to the collaborative instrument guide holder. In certain examples, the method 400 can be broken down into various separate procedures, such as an assembly procedure that can include operations 402-408 and 418, a calibration procedure that can include operations 410-416 and a surgical procedure including operations 420-

428. In each example procedure, certain operations may be optional or may not be performed in the order illustrated in FIG. 17.

At step 402, reaming guide 204 can be attached to robotic arm 120. For example, tool base 202 can be attached to a distal end of robotic arm 120 via insertion of fasteners through mounting bores 234A and 234B, such as after slots 236A and 236B are aligned with pins of robotic arm 120. Main shaft 218 of guide shaft 217 can be inserted into collar 232 of tool base 202 to couple reaming guide 204 to robotic arm 120 via tool base 202. Guide shaft 217 can be threaded into collar 232 or force-fit.

At step 404, reamer 206 can be attached to reaming guide 204. Reamer shaft 210 can be inserted into aperture 244 of collar 222. Reamer shaft 210 can be positioned such that articulating surface 269 of coupler 214 abuts inner surface 242 of collar 222.

At step 406, reamer lock 226 can be assembled to reamer 206. Reamer shaft 210 can be inserted into channel 256 of reamer lock 226. Reamer lock 226 can be slid down reamer shaft 210 until flared portion 230 engages collar 222. As such, articular surface 258 can engage outer surface 240.

At step 408, reamer tracker 304 can be assembled to reamer 206. Sleeve 318 (FIG. 13) can be slid onto reamer shaft 210. As such, reamer tracker 304 can be attached to reamer shaft 210 via arm 316.

At step 410, pointer extension 310 can be assembled to pointer probe 306. With registration pointer 306 assembled to pointer extension 310, such as via engagement of shaft 324 with window 344 (FIG. 16), shaft 334 can be inserted into an opposing pair of receptors 266A-266D. As such, pointer tracker 308 can be attached to reamer shaft 210 via quick-coupling device 264.

At step 412, reamer tracker 304 can be calibrated. Reamer tracker 304 can be calibrated to locate reamer axis 212 in a coordinate system of a robotic surgical system. Reamer tracker 304 can be recognized by a locator of tracking system 165. Thus, the orientation of reamer axis 212 can be known to computing system 140 of robotic system 115.

At step 414, calibrate pointer probe 306 using pointer tracker 308. Pointer tracker 308 can be calibrated to locate center point 272 in the coordinate system of a robotic surgical system. Pointer tracker 308 can be recognized by a locator of tracking system 165. Thus, the position of reamer head 208 can be known to computing system 140 of robotic system 115.

At step 416, pointer extension 310 and pointer probe 306 can be removed from reamer 206. Steps 408-414 can comprise a method for registering a surgical instrument, such as a two-point registration used to locate an orientation (axis) and location (point) of an elongate surgical instrument in a three-dimensional surgical space. Pointer extension 310 and pointer probe 306 can be removed to facilitate performance of a surgical procedure with reamer 206.

At step 418, reamer head 208 can be assembled to reamer shaft 210 of reamer 206. Two of attachment members 260A-260D on the back side of reamer head 208 can be connected to receptors 266A-266D of quick-coupling device 264. As such, center point 272 can be fixed along reamer axis 212.

At step 420, robotic arm 120 can be moved to position reaming guide 204 relative to a patient. Computing system 140 can operate robotic system 115 to move robotic arm 120 according to a surgical plan to align reamer axis 212 relative to a patient.

At step 422, reamer center point 272 can be positioned at a location determined per a surgical plan. Via movement of robotic arm 120 at step 420, center point 272 can be located in a planned location to ream bone along a planned trajectory and to a planned depth.

At step 424, reamer 206 can be moved along reaming axis. Robotic arm 120 can move reamer 206 via reaming guide 204 along reamer axis 212 until center point 272 is located at the desired depth into a bone. During movement of reamer 206 along reamer axis 212, a surgeon can provide motive input to reamer shaft 210, such as at drive lock 312, to cause reamer head 208 remove bone.

At step 426, reamer axis 224 can be articulated using reamer shaft 210. A surgeon can grasp reamer shaft 210 and articulate reamer shaft 210 at center point 272 to change angle 213. Reamer head 208 can be moved to move cutting elements 268A-268G across a bone surface. Thus, the production of tracks from moving cutting elements 268A-268G in single direction can be avoided. Method 400 can return to step 424 and steps 424 and 426 can be repeated until a surgeon is satisfied that the bone is adequately reamed, such as to the planned depth and a desired smoothness. Robotic arm 120 can hold reaming guide 204 in place and lock 226 can prevent reamer 206 from allowing center point 272 from traveling along reaming axis 212 beyond the desired depth of the surgical plan.

At step 428, reamer 206 can be disengaged from the patient. Reamer 206 can be disengaged to allow the surgical procedure to continue. Reamer 206 can be removed from reaming guide 204 and reaming guide 204 can be removed from surgical arm 120 to allow other surgical instruments to be attached to surgical arm 120.

Figure 18:
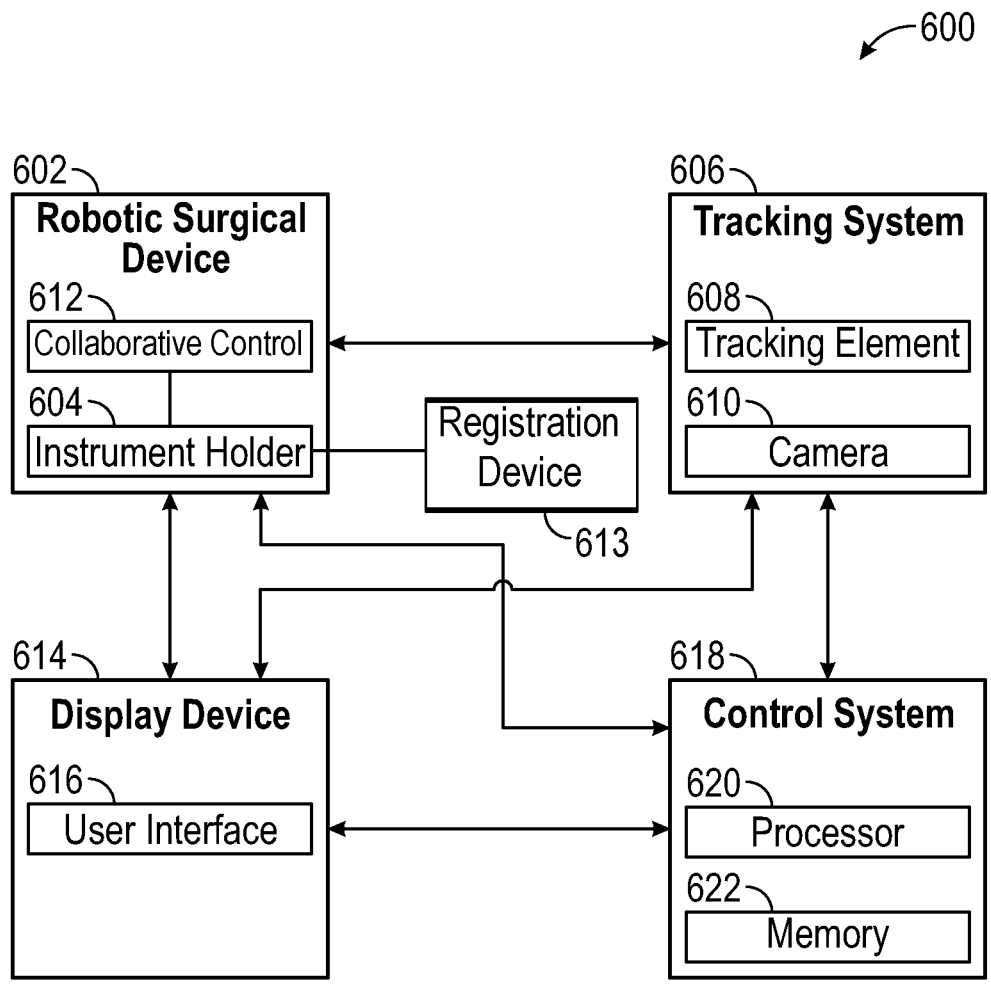
FIG. 18 is a schematic illustration of a robotic surgical system incorporating a collaborative reaming system of the present application interacting with a tracking system.

FIG. 18 illustrates system 600 for performing techniques described herein, in accordance with some embodiments. System 600 is an example of a system that can incorporate surgical system 100 of FIG. 1. System 600 can include robotic surgical device 602 (e.g., robotic surgical device 115) coupled to instrument holder 604 (e.g., reaming guide 204 of reaming system 200), which may interact with tracking system 606. In other examples, the instrument holders described herein can be used without tracking system 606. Tracking system 606 can include tracking element 608 and camera 610. Instrument holder 604 (e.g., reaming guide 204) can include collaborative control 612 (e.g., an articulation coupler comprising collar 222 and coupler 214) and registration device 613 (e.g., registration system 300). System 600 can include display device 614, which can be used to display user interface 616. System 600 can include control system 618 (e.g., a robotic controller or computing system 140 of FIG. 1), including processor 620 and memory 622. In an example, display device 614 can be coupled to one or more of robotic surgical device 602, tracking system 606, or control system 618. As such, data generated by registration device 613 can be shared with control system 618, tracking system 606 and an operator of system 600 via display device 614. In examples, instrument holder 604 can be operated without input from tracking system 608, after a registration process, such that robotic surgical device 602 can be positioned and tracked by movement of robotic arm 120 within the native coordinate system of robotic arm 120. Once in a desired position, collaborative control 612 of robotic surgical device 602 can be freely used by a surgeon without tracking system 606 required to reacquire position information for robotic surgical device and without control system 618 losing track of the location of robotic surgical device 602.

Figure 19:
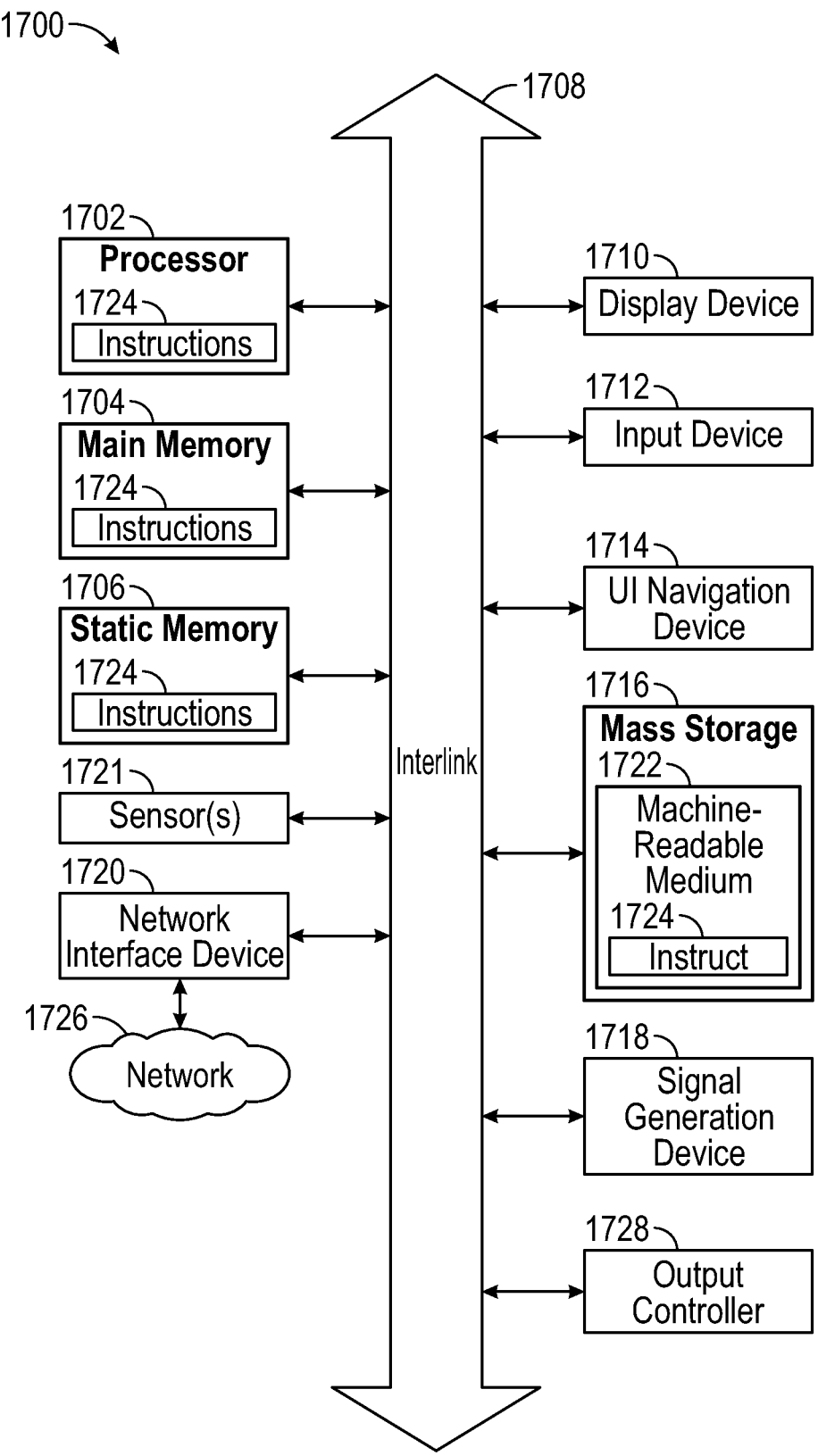
FIG. 19 is a schematic illustration of a block diagram of an example machine upon which any one or more of the techniques discussed herein may be performed and with which any of the devices discussed herein may be used in accordance with some embodiments.

FIG. 19 illustrates a block diagram of an example machine 1700 upon which any one or more of the techniques discussed herein may be performed in accordance with some embodiments. For example, machine 1700 can comprise computing system 140 of FIG. 1. Machine 1700 can comprise an example of a controller for robotic system 115 and sensors 1721 can include tracking elements 304 and 308. As such instructions 1724 can be executed by processor 1702 to generate and correlate position and orientation information to determine the position and orientation of a surgical instrument relative to robotic arm 120. For example, position information of reamer 206 via reamer tracker 304 and pointer tracker 308 (e.g., sensor 1721) relating to the location of reamer head 208 relative to guide shaft 217 can be stored in main memory 1704 and accessed by processor 1702. Processor 1702 can also receive input (such as at input device 1712) relating to the position of reaming guide 204 relative to robotic arm 120 and store such information in main memory 1704. Processor 1702 can further relate position information of reamer head 208 to the position information of arm 120 to correlate the position of reamer head 208 to robotic arm 120 and reaming guide 204. As such, as reamer head 208 moves, machine 1700 can continuously track and update the location of reamer head 208 relative to robotic arm 120 via movement of robotic arm 120 and, for example, display said position on display device 1710 (e.g., user interface devices 145).

In alternative embodiments, machine 1700 may operate as a standalone device or may be connected (e.g., networked) to other machines. In a networked deployment, machine 1700 may operate in the capacity of a server machine, a client machine, or both in server-client network environments. In an example, machine 1700 may act as a peer machine in peer-to-peer (P2P) (or other distributed) network environment. Machine 1700 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Machine (e.g., computer system) 1700 may include hardware processor 1702 (e.g., a central processing unit (CPU), a graphics processing unit (GPU), a hardware processor core, or any combination thereof), main memory 1704 and static memory 1706, some or all of which may communicate with each other via interlink (e.g., bus) 1708. Machine 1700 may further include display unit 1710, alphanumeric input device 1712 (e.g., a keyboard), and user interface (UI) navigation device 1714 (e.g., a mouse). In an example, display unit 1710, input device 1712 and UI navigation device 1714 may be a touch screen display. Machine 1700 may additionally include storage device (e.g., drive unit) 1716, signal generation device 1718 (e.g., a speaker), network interface device 1720, and one or more sensors 1721, such as a global positioning system (GPS) sensor, compass, accelerometer, or other sensor. Machine 1700 may include output controller 1728, such as a serial (e.g., Universal Serial Bus (USB), parallel, or other wired or wireless (e.g., infrared (IR), near field communication (NFC), etc.) connection to communicate or control one or more peripheral devices (e.g., a printer, card reader, etc.).

Storage device 1716 may include machine readable medium 1722 on which is stored one or more sets of data structures or instructions 1724 (e.g., software) embodying or utilized by any one or more of the techniques or functions described herein. Instructions 1724 may also reside, completely or at least partially, within main memory 1704, within static memory 1706, or within hardware processor 1702 during execution thereof by machine 1700. In an example, one or any combination of hardware processor 1702, main memory 1704, static memory 1706, or storage device 1716 may constitute machine readable media.

While machine readable medium 1722 is illustrated as a single medium, the term "machine readable medium" may include a single medium or multiple media (e.g., a centralized or distributed database, and/or associated caches and servers) configured to store the one or more instructions 1724. The term "machine readable medium" may include any medium that is capable of storing, encoding, or carrying instructions for execution by machine 1700 and that cause machine 1700 to perform any one or more of the techniques of the present disclosure, or that is capable of storing, encoding or carrying data structures used by or associated with such instructions. Non-limiting machine readable medium examples may include solid-state memories, and optical and magnetic media.

Instructions 1724 may further be transmitted or received over communications network 1726 using a transmission medium via network interface device 1720 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as Wi-Fi®, IEEE 802.16 family of standards known as WiMax®), IEEE 802.15.4 family of standards, peer-to-peer (P2P) networks, among others. In an example, network interface device 1720 may include one or more physical jacks (e.g., Ethernet, coaxial, or phone jacks) or one or more antennas to connect to communications network 1726. In an example, network interface device 1720 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by machine 1700, and includes digital or analog communications signals or other intangible medium to facilitate communication of such software.

The systems, devices and methods discussed in the present application can be useful in performing robotic-assisted surgical procedures that utilize robotic surgical arms that can be coupled to instrument holders used to precisely align trajectories of instruments relative to anatomy of a patient registered to the space of an operating room. The present disclosure describes adjustable instrument holders that can remain mounted to a robotic surgical arm throughout a surgical procedure. The adjustable instrument holders can be fixed in place for one or more parameters by the robotic surgical arm, but adjusted manually for one or more parameters to facilitate ergonomic operation and execution of surgical technique without removing the instrument holder form the robotic arm. Thus, the adjustable instrument holders can be fixed in place according to particular parameters of a surgical plan (e.g., orientation and depth), but adjusted according to surgeon preference for other parameters (e.g., orientation and rotation).

EXAMPLES

Example 1 can include or use subject matter such as a reamer attachment system for attaching a reamer to a robotic arm, the reamer attachment system can comprise a reaming guide comprising a guide shaft and a collar attached to the guide shaft, a reamer shaft extending through the collar and configured to articulate against the collar, and a reamer lock couplable to the reamer shaft to engage the collar and prevent axial displacement of the reamer shaft relative to the collar while permitting the reamer shaft to articulate against the collar.

Example 2 can include, or can optionally be combined with the subject matter of Example 1, to optionally include a collar of the reaming guide that can comprise a ring-shaped body disposed about a center point, an inner articulating surface on the ring-shaped body, and an outer articulating surface on the ring-shaped body.

Example 3 can include, or can optionally be combined with the subject matter of one or any combination of Examples 1 or 2 to optionally include an inner articulating surface and an outer articulating surface that are segments of a spherical body.

Example 4 can include, or can optionally be combined with the subject matter of one or any combination of Examples 1 through 3 to optionally include a guide shaft that can comprise an attachment shaft portion extending from the outer articulating surface, and a main shaft portion extending from the attachment shaft portion at an angle along a guide axis.

Example 5 can include, or can optionally be combined with the subject matter of one or any combination of Examples 1 through 4 to optionally include a collar of the reaming guide that can further comprise a proximal end connecting the inner articulating surface and the outer articulating surface, and a distal end connecting the inner articulating surface and the outer articulating surface, wherein the proximal and distal ends are spaced along an articulation axis that extends through the center point and the guide axis extends at an angle relative to the articulation axis in a range of approximately five degrees to approximately twenty-five degrees.

Example 6 can include, or can optionally be combined with the subject matter of one or any combination of Examples 1 through 5 to optionally include a reamer lock that can comprise a tubular body configured to extend along the reamer shaft, and a flared portion extending from a distal end of the tubular body and configured to engage the outer articulating surface.

Example 7 can include, or can optionally be combined with the subject matter of one or any combination of Examples 1 through 6 to optionally include a reamer shaft that can further comprise a quick-coupling device located at a distal end of the reamer shaft;

Example 8 can include, or can optionally be combined with the subject matter of one or any combination of Examples 1 through 7 to optionally include a reamer head couplable to the quick-coupling device, and a pointer probe couplable to the quick-coupling device that can comprise a tracking element, a probe shank extending from the tracking element, and a probe extension coupled to the probe shank, the probe extension comprising an elongate shaft for attaching to the quick-coupling device.

Example 9 can include or use subject matter such as a robotic surgical system that can comprise an articulatable arm configured to move a distal end of the articulatable arm to a location in a coordinate system for the robotic surgical system, and a surgical instrument coupler connected to the distal end of the articulatable arm that can comprise a guide shaft extending from the distal end, an articulation coupler connected to the guide shaft at a fixed location relative to the distal end, the articulation coupler defining a pivot center, an instrument shaft connected to the articulation coupler to pivot about the pivot center, and a lock coupled to the instrument shaft to constrain axial movement of the shaft relative to the articulation coupler.

Example 10 can include, or can optionally be combined with the subject matter of Example 9, to optionally include a an articulation coupler that can comprise a collar connected to the guide shaft, the collar including an opening to receive the instrument shaft, and a lock that can comprise a tubular body configured to extend along the instrument shaft, and a flared portion extending from an end of the tubular body and configured to engage the collar.

Example 11 can include, or can optionally be combined with the subject matter of one or any combination of Examples 9 or 10 to optionally include an articulation coupler that can comprise a collar connected to the guide shaft that can comprise a first curved articulation surface, and an instrument shaft that can comprise a guide stop comprising a second curved articulation surface configured to articulate against the first curved articulation surface.

Example 12 can include, or can optionally be combined with the subject matter of one or any combination of Examples 9 through 11 to optionally include first and second curved articulation surfaces that are spherical.

Example 13 can include, or can optionally be combined with the subject matter of one or any combination of Examples 9 through 12 to optionally include an articulation coupler that is angled relative to the articulatable arm such that the instrument shaft extends at an angle relative to the guide shaft in a range of approximately five degrees to approximately twenty-five degrees.

Example 14 can include, or can optionally be combined with the subject matter of one or any combination of Examples 9 through 13 to optionally include an instrument shaft that can further comprise a quick-coupling device located at a distal end of the instrument shaft.

Example 15 can include, or can optionally be combined with the subject matter of one or any combination of Examples 9 through 14 to optionally include a reamer head couplable to the quick-coupling device, and a tracking element couplable to the quick-coupling device to register the instrument shaft to the coordinate system for the robotic surgical system.

Example 16 can include or use subject matter such as a method for collaborative reaming of a bone socket between a surgical robot and a surgeon that can comprise positioning a reamer guide at a location in a coordinate system for the surgical robot system using a robotic arm of the surgical robot, coupling a reamer to the reamer guide such that a reamer axis passes through the location, constraining movement of the reamer along the reamer axis, and pivoting the reamer at the location to remove bone.

Example 17 can include, or can optionally be combined with the subject matter of Example 16, to optionally include coupling the reamer to the reamer guide comprises inserting a reamer shaft of the reamer through an opening in a collar of an articulation coupler.

Example 18 can include, or can optionally be combined with the subject matter of one or any combination of Examples 16 or 17 to optionally include coupling the reamer to the reamer guide by engaging a first spherical articulating surfaces of a stop located on the reamer shaft with a second spherical articulating surface of located on the articulation coupler.

Example 19 can include, or can optionally be combined with the subject matter of one or any combination of Examples 16 through 18 to optionally include constraining movement of the reamer along the reamer axis by positioning a lock on the reamer shaft against the collar to constrain axial movement of the reamer.

Example 20 can include, or can optionally be combined with the subject matter of one or any combination of Examples 16 through 19 to optionally include pivoting the reamer at the location to remove bone by manually moving the reamer shaft to guide a reamer head through a reaming pattern.

Example 21 can include or use subject matter such as a pointer probe couplable to a quick-coupling device of an instrument shaft that can comprise a tracking element, a probe shank extending from the tracking element, the probe shank including a first pointed tip, and a probe extension coupled to the probe shank that can comprise an elongate shaft for attaching to the quick-coupling device, a first end including a socket for receiving the first pointed tip, and a second end including a second pointed tip.

Each of these non-limiting examples can stand on its own, or can be combined in various permutations or combinations with one or more of the other examples.

VARIOUS NOTES

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventor also contemplates examples in which only those elements shown or described are provided. Moreover, the present inventor also contemplates examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A reamer attachment system for attaching a reamer to a robotic arm, the reamer attachment system comprising:
   a reaming guide comprising:
      a guide shaft;
      a collar attached to the guide shaft; and
      a tool base connected to the guide shaft opposite the collar configured to attach to a distal end of a robotic surgical arm;
   a reamer shaft extending into the collar, the reamer shaft configured to articulate against the collar; and
   a reamer lock couplable to the reamer shaft to engage the collar and prevent axial displacement of the reamer shaft relative to the collar while permitting the reamer shaft to articulate against the collar.

2. The reamer attachment system of claim 1, wherein the collar of the reaming guide comprises:
a ring-shaped body disposed about a center point;
an inner articulating surface on the ring-shaped body; and
an outer articulating surface on the ring-shaped body.

3. The reamer attachment system of claim 2, wherein the inner articulating surface and the outer articulating surface are segments of a spherical body.

4. The reamer attachment system of claim 2, wherein the guide shaft comprises:
an attachment shaft portion extending from the outer articulating surface; and
a main shaft portion extending from the attachment shaft portion at an angle along a guide axis.

5. The reamer attachment system of claim 4, wherein:
the collar of the reaming guide further comprises:
a proximal end connecting the inner articulating surface and the outer articulating surface; and
a distal end connecting the inner articulating surface and the outer articulating surface;
wherein the proximal end and the distal end are spaced along an articulation axis that extends through the center point; and
the guide axis extends at an angle relative to the articulation axis in a range of approximately five degrees to approximately twenty-five degrees.

6. The reamer attachment system of claim 2, wherein the reamer lock comprises:
a tubular body configured to extend along the reamer shaft; and
a flared portion extending from a distal end of the tubular body and configured to engage the outer articulating surface.

7. The reamer attachment system of claim 2, wherein the reamer shaft further comprises a quick-coupling device located at a distal end of the reamer shaft.

8. The reamer attachment system of claim 7, further comprising:
a reamer head couplable to the quick-coupling device; and
a pointer probe couplable to the quick-coupling device, the pointer probe comprising:
a tracking element;
a probe shank extending from the tracking element, and
a probe extension coupled to the probe shank, the probe extension comprising an elongate shaft for attaching to the quick-coupling device.

9. The reamer attachment system of claim 1, wherein:
the guide shaft extends along a guide axis,
the collar is attached to the guide shaft at a fixed location relative to the guide shaft and the collar defines a pivot center located on the guide axis;
the reamer shaft extends along a reamer axis;
the reamer shaft is configured to articulate against the collar such that the reamer axis can be varied relative to the guide axis; and
the reamer lock prevents axial displacement of the reamer shaft relative to the collar along the reamer axis.

10. The reamer attachment system of claim 1, wherein the tool base comprises:
a plate for mounting to the distal end of the robotic surgical arm;
one or more mounting bores for receiving a fastener; and
one or more alignment slots for mating with an alignment feature of the robotic surgical arm.

11. A surgical instrument coupler comprising:
a guide shaft extending along a guide axis;
an articulation coupler connected to the guide shaft at a fixed location relative to the guide shaft, the articulation coupler comprising a collar connected to the guide shaft, the collar comprising a first curved articulation surface defining a pivot center located on the guide axis;
an instrument shaft extending along an instrument axis connected to the articulation coupler to pivot about the pivot center such that the instrument axis can be varied relative to the guide axis, the instrument shaft comprising a guide stop comprising a second curved articulation surface configured to articulate against the first curved articulation surface; and
a lock coupled to the instrument shaft to constrain axial movement of the instrument shaft along the instrument axis relative to the articulation coupler.

12. The surgical instrument coupler of claim 11, wherein:
the articulation coupler comprises:
a collar connected to the guide shaft, the collar including an opening to receive the instrument shaft; and
the lock comprises:
a tubular body configured to extend along the instrument shaft; and
a flared portion extending from an end of the tubular body and configured to engage the collar.

13. The surgical instrument coupler of claim 11, wherein the first curved articulation surface and the second curved articulation surface are spherical.

14. The surgical instrument coupler of claim 11, wherein the articulation coupler is angled relative to the guide shaft such that the instrument shaft extends at an angle relative to the guide shaft in a range of approximately five degrees to approximately twenty-five degrees.

15. The surgical instrument coupler of claim 11, wherein the instrument shaft further comprises:
a quick-coupling device located at a distal end of the instrument shaft.

16. The surgical instrument coupler of claim 15, further comprising:
a reamer head couplable to the quick-coupling device; and
a tracking element couplable to the quick-coupling device to register the instrument shaft to a coordinate system for a robotic surgical system.

17. The surgical instrument coupler of claim 11, further comprising a pointer probe couplable to a quick-coupling device of the instrument shaft, the pointer probe comprising:
a tracking element;
a probe shank extending from the tracking element, the probe shank including a first pointed tip; and
a probe extension coupled to the probe shank, the probe extension comprising:
an elongate shaft for attaching to the quick-coupling device;
a first end including a socket for receiving the first pointed tip; and
a second end including a second pointed tip.

18. A reamer attachment system for attaching a reamer to a robotic arm, the reamer attachment system comprising:
a surgical instrument coupler for connecting to a distal end of the robotic arm, the surgical instrument coupler comprising:
a guide shaft extending from the distal end;
an articulation coupler connected to the guide shaft at a fixed location relative to the distal end, the articulation coupler defining a pivot center;

an instrument shaft connected to the articulation coupler to pivot about the pivot center, the instrument shaft comprising a quick-coupling device located at a distal end of the instrument shaft; and a lock coupled to the instrument shaft to constrain axial movement of the instrument shaft relative to the articulation coupler;

a reamer head couplable to the quick-coupling device; and a pointer probe couplable to the quick-coupling device, the pointer probe comprising:

a tracking element;

a probe shank extending from the tracking element; and a probe extension coupled to the probe shank, the probe extension comprising an elongate shaft for attaching to the quick-coupling device.

* * * * *